United States Patent
Noelle

(10) Patent No.: US 10,858,439 B2
(45) Date of Patent: *Dec. 8, 2020

(54) ANTI-CD154 ANTIBODIES HAVING IMPAIRED FCR BINDING AND/OR COMPLEMENT BINDING PROPERTIES AND RELATED THERAPIES

(71) Applicant: THE TRUSTEES OF DARTMOUTH COLLEGE, Hanover, NH (US)

(72) Inventor: Randolph J. Noelle, Plainfield, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/383,745

(22) Filed: Apr. 15, 2019

(65) Prior Publication Data

US 2019/0309081 A1 Oct. 10, 2019

Related U.S. Application Data

(60) Division of application No. 15/074,505, filed on Mar. 18, 2016, now Pat. No. 10,259,879, which is a division of application No. 13/648,808, filed on Oct. 10, 2012, now Pat. No. 9,321,833, which is a continuation-in-part of application No. 13/439,186, filed on Apr. 4, 2012, now Pat. No. 8,852,597.

(60) Provisional application No. 61/471,287, filed on Apr. 4, 2011.

(51) Int. Cl.
| | | |
|---|---|---|
| *A61K 39/395* | (2006.01) | |
| *C07K 16/28* | (2006.01) | |
| *C07K 16/18* | (2006.01) | |
| *A61K 39/00* | (2006.01) | |

(52) U.S. Cl.
CPC .......... *C07K 16/2875* (2013.01); *C07K 16/18* (2013.01); *A61K 2039/505* (2013.01); *C07K 2317/24* (2013.01); *C07K 2317/41* (2013.01); *C07K 2317/52* (2013.01); *C07K 2317/565* (2013.01); *C07K 2317/71* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 9,028,826 B2* | 5/2015 | Noelle | C07K 16/2875 |
| | | | 424/154.1 |
| 9,321,833 B2* | 4/2016 | Noelle | C07K 16/2875 |
| 9,758,857 B2* | 9/2017 | Nagamine | C23C 14/35 |
| 2004/0110226 A1* | 6/2004 | Lazar | C07K 16/00 |
| | | | 435/7.1 |

OTHER PUBLICATIONS

Jefferis.Nature Reviews / Drug Discovery 8: 226-234, Mar. 2009; Glycosylation as a Strategy to Improve Antibody-Based Therapeutics (Year: 2009).*

Kiyoshi et al, .Scientific Reports (2018) 8:3955 pp. 1-11, DOI:10.1038/s41598-018-22199-8; Assessing the Heterogeneity of the Fc-Glycan of a Therapeutic Antibody Using an Engineered FcγReceptor IIIa-Immobilized Column (Year: 2018).*

Wang et al.,Protein Cell 9: 63-73, 2018; DOI 10.1007/s13238-017-473-8; IgG Fc engineering to modulate antibody effector functions (Year: 2018).*

Saunders et al., Conceptual Approaches to Modulating Antibody Effector Functions and Circulating Half-Life (Frontiers in Immunology; 10:1-20, 2019; doi: 10.3389/fimmu.2019.01296. (Year: 2019).*

* cited by examiner

*Primary Examiner* — Phillip Gambel
(74) *Attorney, Agent, or Firm* — Robin L. Teskin; Baker, Donelson, Bearman, Caldwell & Berkowitz PC

(57) ABSTRACT

Improved anti-CD154 antibodies are provided herein which have ablated FcR binding and/or complement binding/activation. The use of these antibodies for inducing tolerance and treating immune diseases including autoimmunity, inflammation and allergic disorders is disclosed herein.

12 Claims, 18 Drawing Sheets

Specification includes a Sequence Listing.

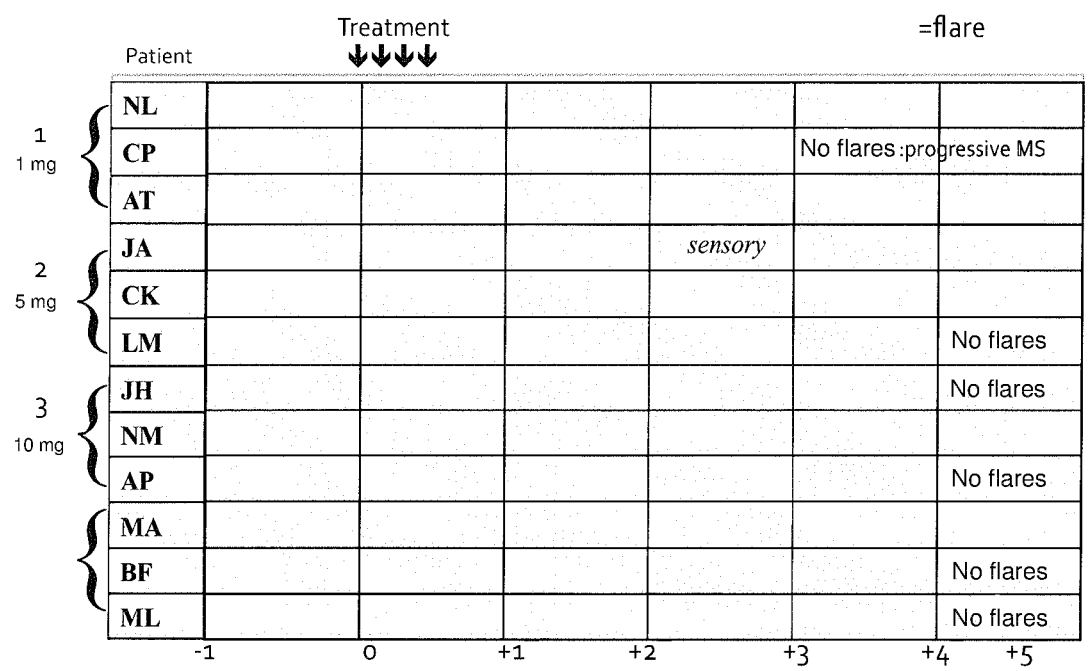
Figure 1. Impact of αCD154 therapy on relapse rate in RR MS Patients.

Hamster Antibody Kappa cDNA Sequence

Gaagcatcatcagacaggcactggagcaaaatggagtcacacaatgaggtccttgtgaccctgctgctctgggtgtctggtgcc
tgtgcagatatcgtgctgacacagtctccatcttccttggctgtgtccgcaggagacaaggtcaccatcaactgcaagtccagtca
gagtcttttatctggtggctataactacttggcttggtaccagcagaaaacagggcagtctcctaaattactgatctatttcacatcca
ctcggcacactggtgtccctgatcgcttcataggcagtgggtctgggacagatttcactctaaccatcaacagtttccagactgag
gatctgggagattactattgtcagcatcattacggtactcctctcacgttcggtgatggcaccaagctggagataaaacgggctga
tgctaagccaaccgtctccatcttcccaccatccagtgagcagttgggcactggaagtgccacacttgtgtgcttcgtgaacaact
tctaccccaaagacatcaatgtcaagtggaaagtagatggcagtgaaaaacgagatggcgtcctgcagagtgtcactgatcagg
acagcaaagacagcacctacagcctgagcagcaccctctcgctgaccaaagcagattatgagaggcataacctgtatacctgtg
aggttactcataagacatcaactgcagccattgtcaagaccctgaacaggaatgagtgttagagcagaggtcctgaggcacca
ccacctgctccctaggaccattctcagtcttccctcctaaggtcttggagctttcttcatagacaacctaccactgttgcagtcctcca
aaccccaccacctcatctccctcccttcttggctttatcatgctaatatttggggaagatattgaataaagtgaatcattgcactt
g

Hamster Antibody Heavy Chain cDNA Sequence gaacatgttatcagtgtgctctccacagtcactgagcacacaggtcttcaccatggtatggggcttgatcatcatcttcctggtcaca
gcaggtacaggtgtccactcccaggtccagttgaagcagtctgggggctgagtttgtgaagcctggagcctcagtgaagatatcct
gcaaaacttcaggctataccttcactgatggctacatgaactgggttgagcagaagcctgggcagggccttgagtggattggaa
gaattgatcctgatagtggtgatactaggtacaatcagaagttccagggcaaggccacactgactagagacaaatcctccagca
cagtctacatggacctcaggagtctgacatctgaggactctgctgtctattactgtgcgagagcccccttatatagcggatataggg
gaggcctttgattactggggccaaggaaccatggtcaccgtctcctcagctggaagaacagccccatctgtctatcccttggccc
ctgcctgtgacagcacaaccagcaccacggacacggtgaccctgggatgcctggtcaagggctatttccctgagccggtgacc
gtaagctggaactctggagccctgaccagcggtgtgcacaccttcccatctgtcctgcgttctgggctctactccctcagcagctc
agtgactgtatcttccagcacctggcccagccagactatc

Figure 2. Nucleotide sequence of hamster anti-murine CD154. Shown are the k and heavy chain sequence for the MR1 hamster IgG1.

| Variant | Binding of human IgG1 variants to human FcRs and FcRn (% binding compared to WT IgG1) | | | | |
| --- | --- | --- | --- | --- | --- |
| | FcRn | FcγRI | FcγRIIA | FcγRIIB | FcγRIIIA |
| E233P | 0.54 | 0.12 | 0.08 | 0.12 | 0.04 |

Figure 3. Reductions in FcR binding in the E233P IgG1 variant.

FIGURE 4: Tested mutations in MR1 which ablate C1q binding.

Figure 5. Loss of complement activation does not reduce the ability of anti-CD40L to induce tolerance.
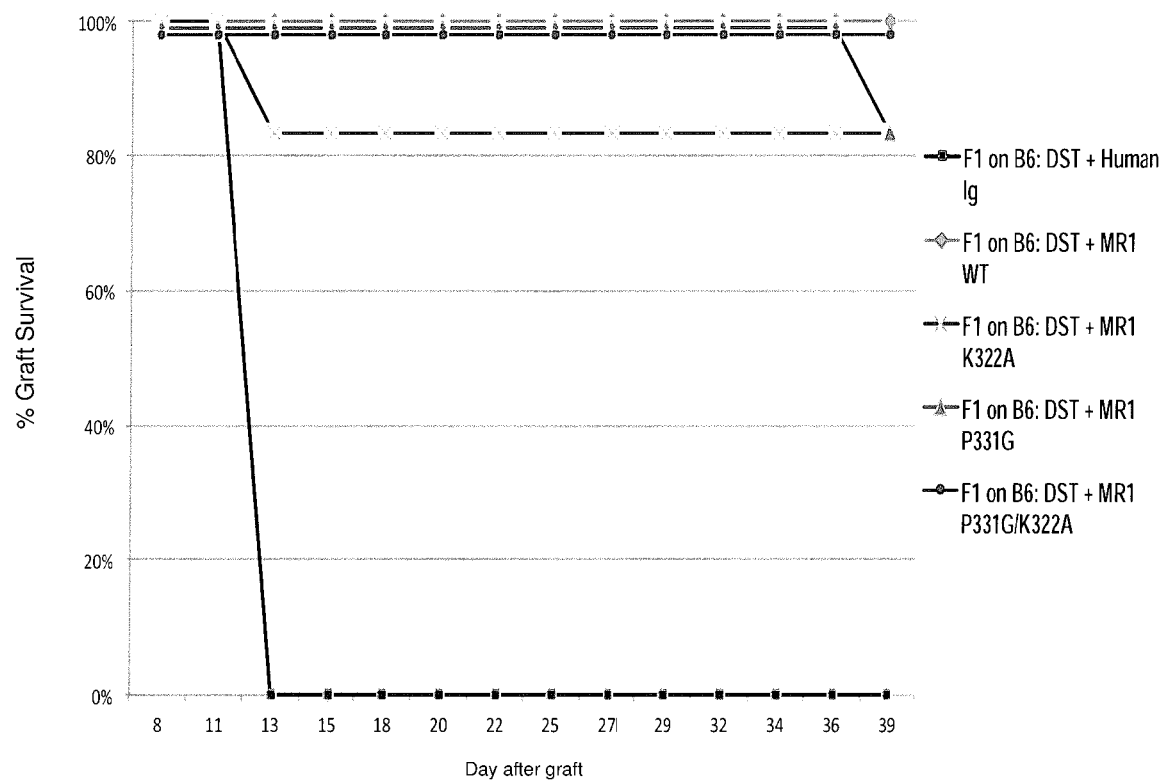

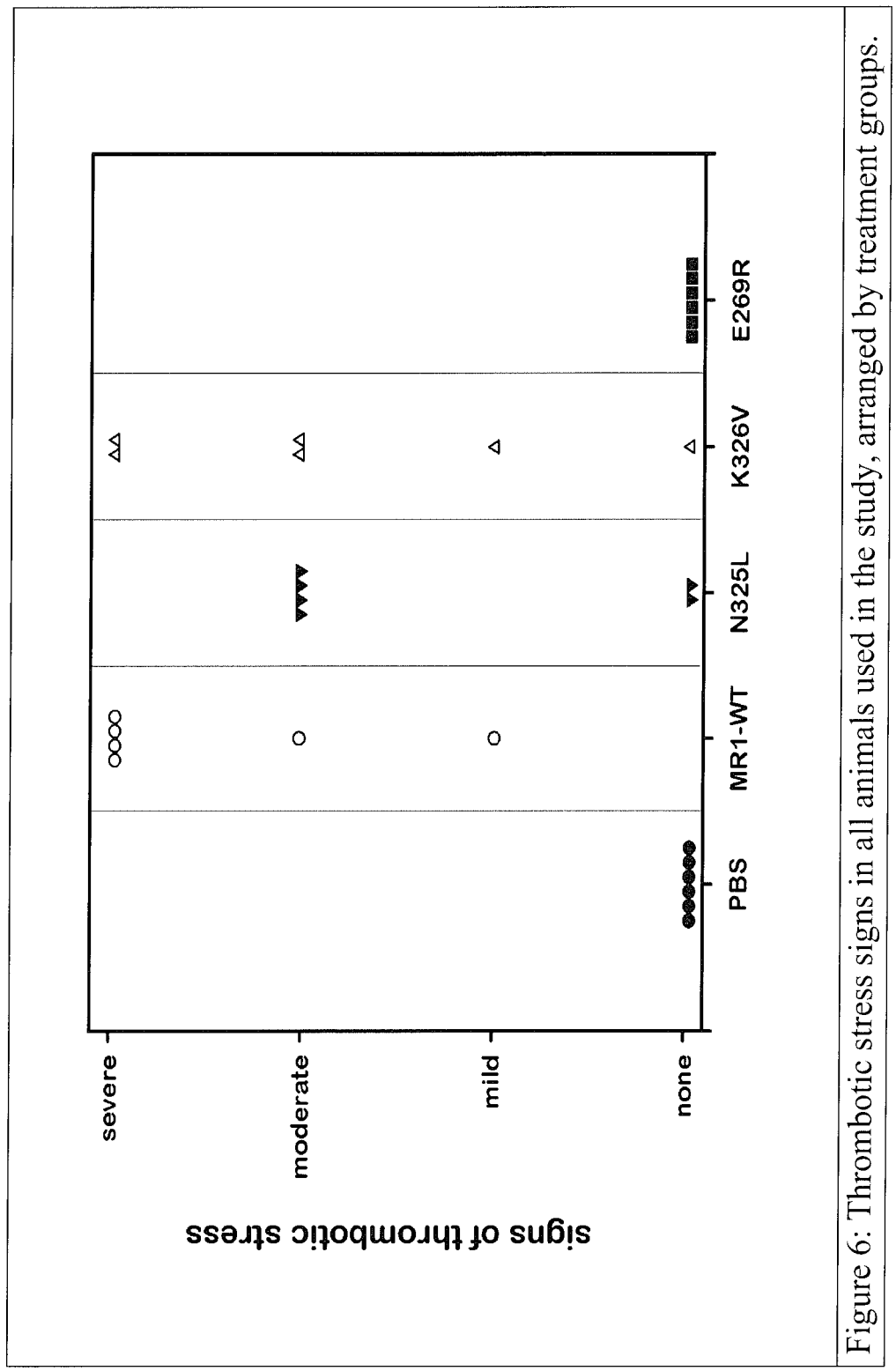
Figure 6: Thrombotic stress signs in all animals used in the study, arranged by treatment groups.

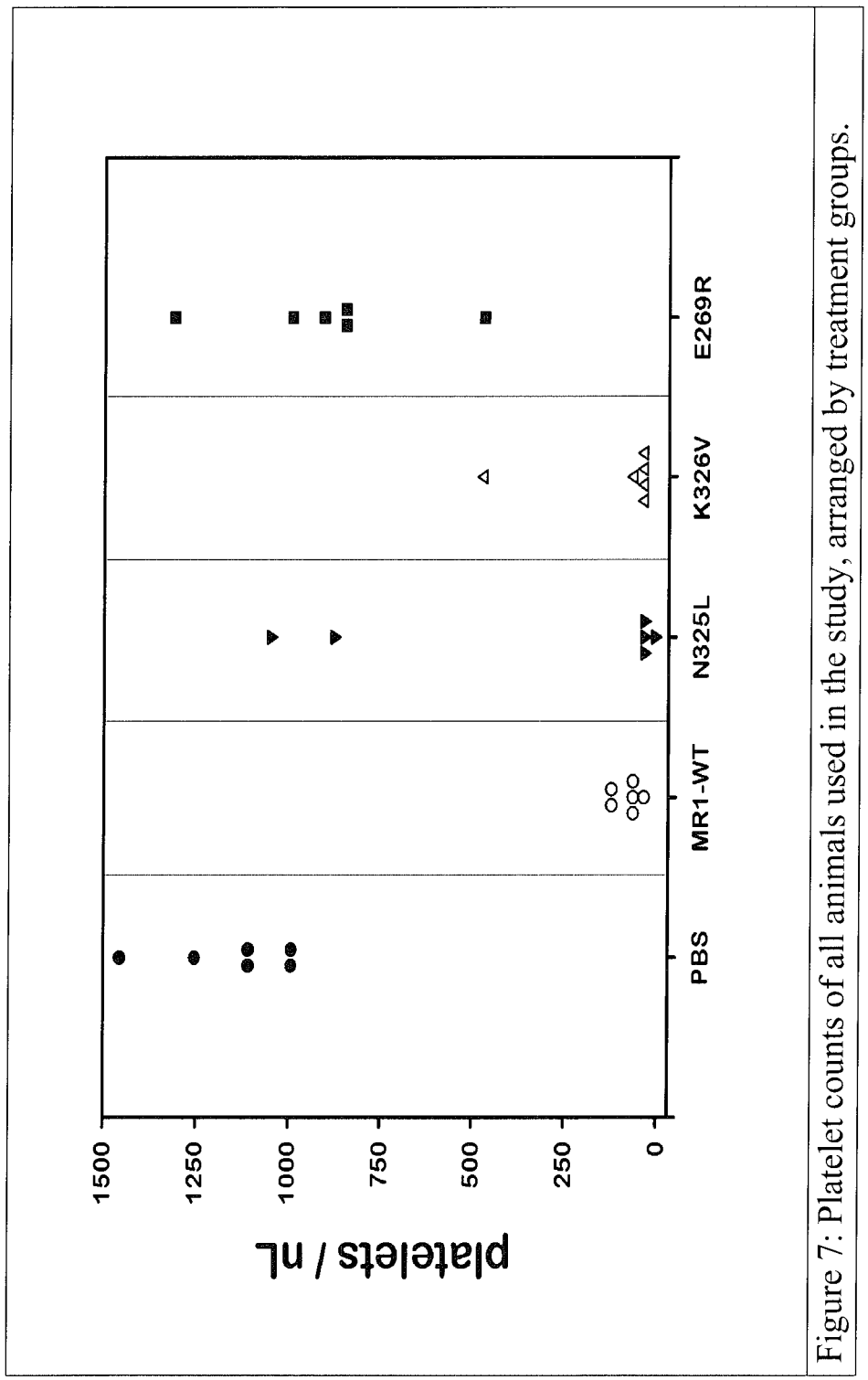
Figure 7: Platelet counts of all animals used in the study, arranged by treatment groups.

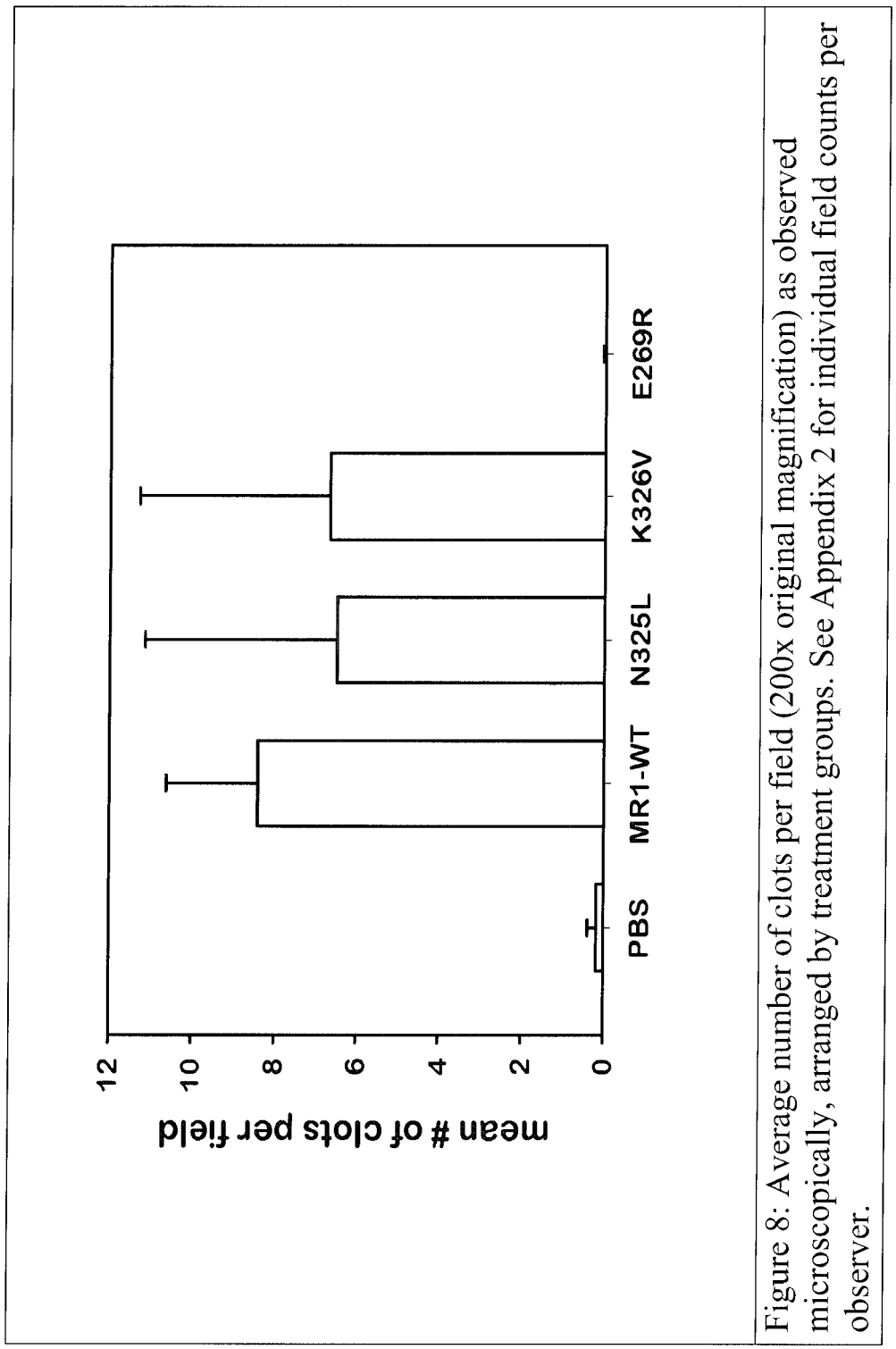
Figure 8: Average number of clots per field (200x original magnification) as observed microscopically, arranged by treatment groups. See Appendix 2 for individual field counts per observer.

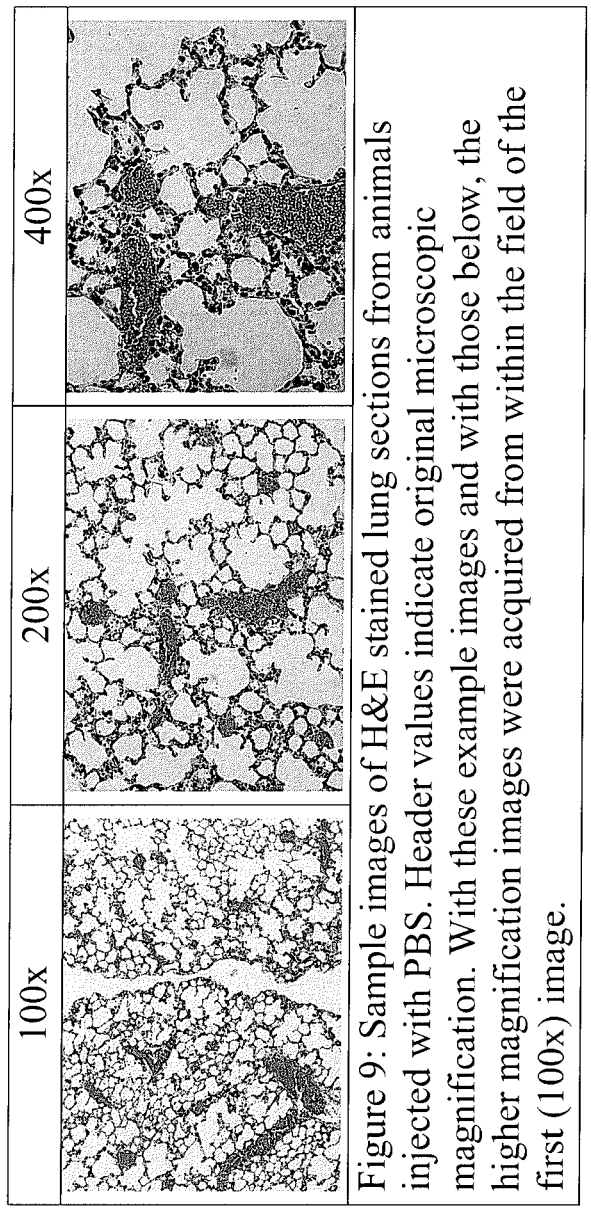
Figure 9: Sample images of H&E stained lung sections from animals injected with PBS. Header values indicate original microscopic magnification. With these example images and with those below, the higher magnification images were acquired from within the field of the first (100x) image.

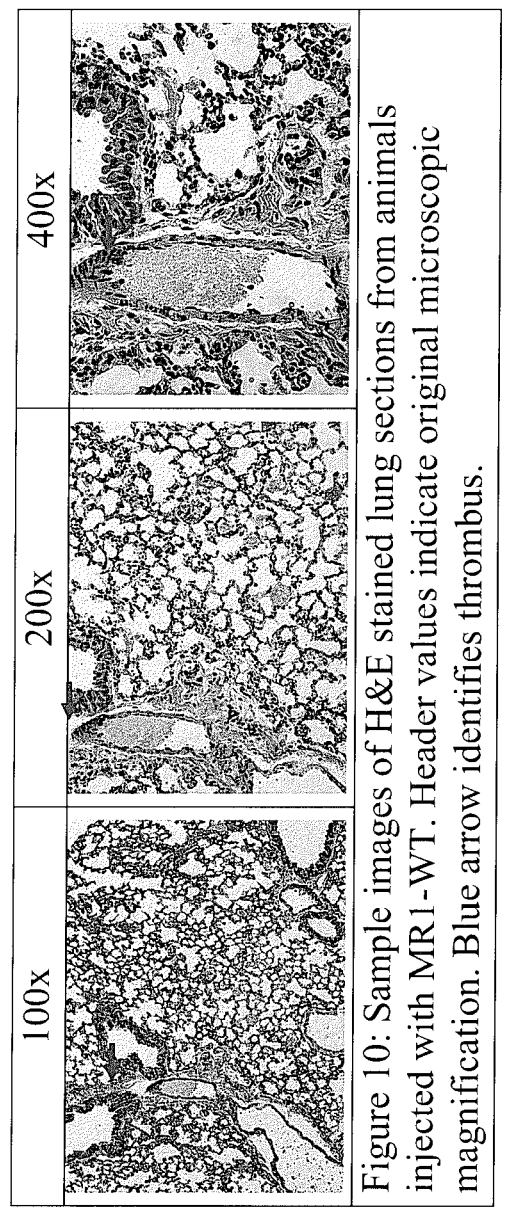
Figure 10: Sample images of H&E stained lung sections from animals injected with MR1-WT. Header values indicate original microscopic magnification. Blue arrow identifies thrombus.

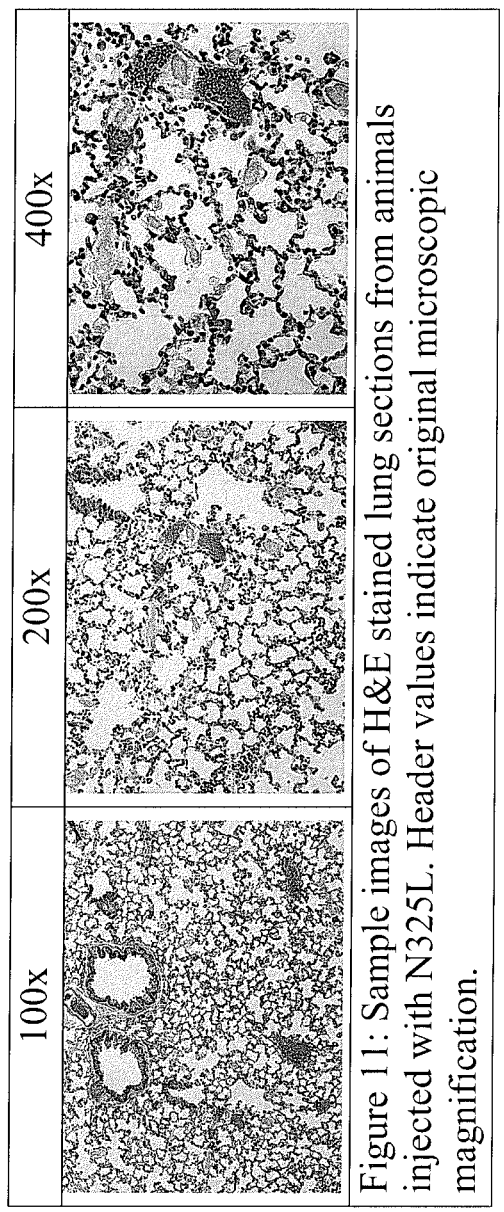
Figure 11: Sample images of H&E stained lung sections from animals injected with N325L. Header values indicate original microscopic magnification.

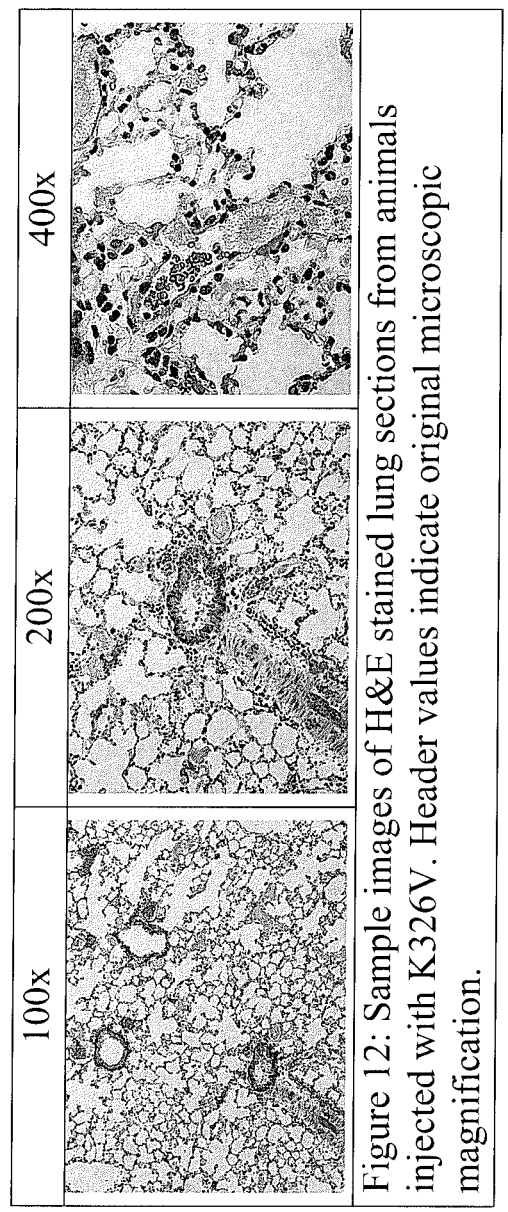
Figure 12: Sample images of H&E stained lung sections from animals injected with K326V. Header values ind

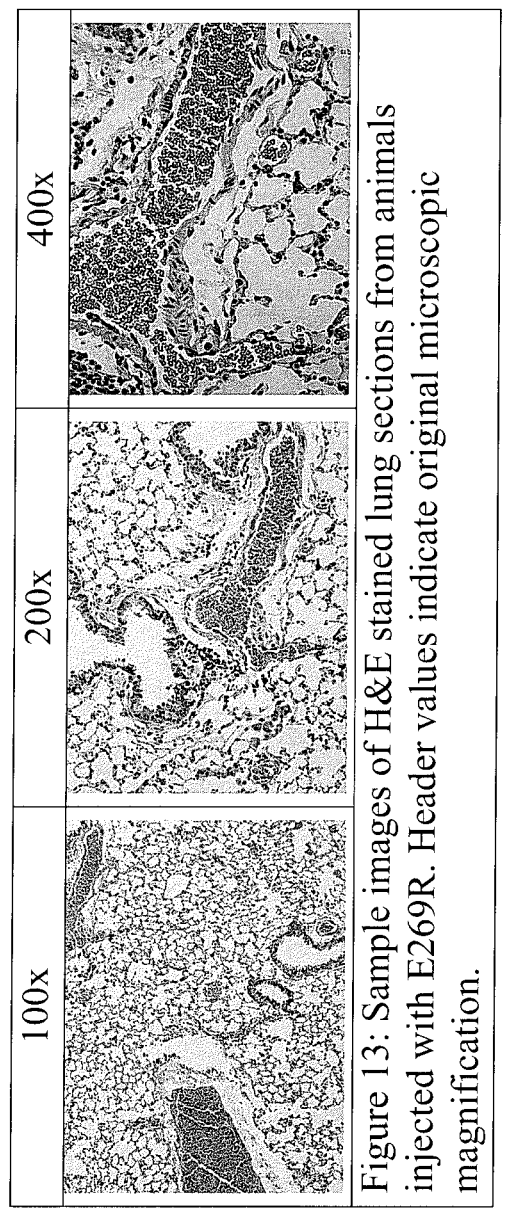
Figure 13: Sample images of H&E stained lung sections from animals injected with E269R. Header values indicate original microscopic magnification.

24-31 Humanized V_L #1

```
     BglII        9              18              27              36              45              54
5' AGA TCT CTC ACC ATG GGC TTC AAG ATG GAG TCA CAG TTT CTG GCC TTT GTA TTC
                   M   G   F   K   M   E   S   Q   F   L   A   F   V   F 63              72              81    FR1 90              99             108
   GCG TTT CTC TGG TTG TCT GGT GTT GAT GGA GAC ATT GTG ATG ACC CAG TCT CCA
    A   F   L   W   L   S   G   V   D   G   D   I   V   M   T   Q   S   P 117             126             135             144             153 CDR1    162
   TCT TTC CTC TCC GCC TCC GTA GGA GAC AGG GTC ACC ATC ACC TGC AAG GCC AGT
    S   F   L   S   A   S   V   G   D   R   V   T   I   T   C   K   A   S 171             180             189 FR2 198             207             216
   CAG AAT GTG ATT ACT GCT GTA GCC TGG TAT CAA CAG AAA CCA GGA AAG TCT CCT
    Q   N   V   I   T   A   V   A   W   Y   Q   Q   K   P   G   K   S   P 225             234 CDR2 243             252 FR3 261             270
   AAA TTG CTG ATT TAC TCG GCA TCC AAT CGG TAC ACT GGA GTC CCT GAT CGC TTC
    K   L   L   I   Y   S   A   S   N   R   Y   T   G   V   P   D   R   F 279             288             297             306             315             324
   TCA GGC AGT GGG TCT GGG ACA GAT TTC ACT CTC ACC ATC AGC TCT CTC CAG CCA
    S   G   S   G   S   G   T   D   F   T   L   T   I   S   S   L   Q   P 333             342             351 CDR3 360             369             378
   GAA GAC TTC GCA GAT TAT TTC TGC CAG CAA TAT AAC AGC TAT CCG TAC ACG TTC
    E   D   F   A   D   Y   F   C   Q   Q   Y   N   S   Y   P   Y   T   F

FR4     387             396             405    BsiWI
   GGA GGG GGG ACC AAG CTG GAA ATC AAA CGT ACG 3'
    G   G   G   T   K   L   E   I   K   R   T
```

FIGURE 14

24-31 Humanized $V_L$ #2

```
      BglII         9              18              27              36              45              54
5'   AGA TCT CTC ACC ATG GGC TTC AAG ATG GAG TCA CAG TTT CTG GCC TTT GTA TTC
     --- --- --- --- --- --- --- --- --- --- --- --- --- --- --- --- --- ---
                     M   G   F   K   M   E   S   Q   F   L   A   F   V   F 63              72              81           90 FR1          99             108
     GCG TTT CTC TGG TTG TCT GGT GTT GAT GGA GAC ATT GTG ATG ACC CAG TCT CCA
     --- --- --- --- --- --- --- --- --- --- --- --- --- --- --- --- --- ---
      A   F   L   W   L   S   G   V   D   G | D   I   V   M   T   Q   S   P 117             126             135             144            153 CDR1    162
     GAT TCT CTC GCC GTG TCC CTC GGA GAG AGG GCC ACC ATC AAC TGC AAG GCC AGT
     --- --- --- --- --- --- --- --- --- --- --- --- --- --- --- --- --- ---
      D   S   L   A   V   S   L   G   E   R   A   T   I   N   C | K   A   S 171             180          189 FR2   198             207             216
     CAG AAT GTG ATT ACT GCT GTA GCC TGG TAT CAA CAG AAA CCA GGA CAA TCT CCT
     --- --- --- --- --- --- --- --- --- --- --- --- --- --- --- --- --- ---
      Q   N   V   I   T   A   V   A | W   Y   Q   Q   K   P   G   Q   S   P 225         234 CDR2    243          252 | FR3   261             270
     AAA TTG CTG ATT TAC TCG GCA TCC AAT CGG TAC ACT GGA GTC CCT GAT CGC TTC
     --- --- --- --- --- --- --- --- --- --- --- --- --- --- --- --- --- ---
      K   L   L   I   Y | S   A   S   N   R   Y   T   G   V   P   D   R   F 279             288             297             306             315            324
     TCA GGC AGT GGG TCT GGG ACA GAT TTC ACT CTC ACC ATC AGC TCT CTC CAG GCC
     --- --- --- --- --- --- --- --- --- --- --- --- --- --- --- --- --- ---
      S   G   S   G   S   G   T   D   F   T   L   T   I   S   S   L   Q   A 333             342         351 CDR3    360             369            378
     GAA GAC GTG GCA GAT TAT TTC TGC CAG CAA TAT AAC AGC TAT CCG TAC ACG TTC
     --- --- --- --- --- --- --- --- --- --- --- --- --- --- --- --- --- ---
      E   D   V   A   D   Y   F | C   Q   Q   Y   N   S   Y   P   Y   T | F

FR4  387             396         405  BsiWI
     GGA GGG GGG ACC AAG CTG GAA ATC AAA CGT ACG 3'
     --- --- --- --- --- --- --- --- --- --- ---
      G   G   G   T   K   L   E   I   K   R   T
```

FIGURE 15

24-31 Humanized V$_H$ #1

```
     SalI       9              18              27              36              45              54
5'  GTC GAC  ATG ATG GTG TTA AGT CTT CTG TAC CTG TTG ACA GCC CTT CCG GGT TTC
              M   M   V   L   S   L   Y   L   L   T   A   L   P   G   F

63  FR1      72              81              90              99             108
    CTG TCA  GAG GTG CAG CTT CAG GAG TCA GGA CCT GGC CTC GTG AAA CCT TCT GAG
     L   S    E   V   Q   L   Q   E   S   G   P   G   L   V   K   P   S   E 117             126             135             144             153 CDR1        162
    ACT CTG TCC CTC ACC TGT ACC GTC TCT GGC GAC TCC ATC ACT AAT GGT TTC TGG
     T   L   S   L   T   C   T   V   S   G   D   S   I   T   N   G   F   W

171 FR2         180             189             198             207 CDR2        216
    ATC TGG ATC CGG AAA CCA CCA GGG AAT AAA CTT GAG TAC ATG GGC TAC ATA AGT
     I   W   I   R   K   P   P   G   N   K   L   E   Y   M   G   Y   I   S 225             234             243             252             261 FR3         270
    TAC AGT GGT AGC ACT TAC TAC AAT CCA TCT CTC AAG AGT CGA ATC TCC ATC TCT
     Y   S   G   S   T   Y   Y   N   P   S   L   K   S   R   I   S   I   S 279             288             297             306             315             324
    CGC GAC ACA TCC AAG AAC CAG TTC TCT CTA AAG TTG TCT TCT GTG ACT GCC GCC
     R   D   T   S   K   N   Q   F   S   L   K   L   S   S   V   T   A   A 333             342             351 CDR3        360             369             378
    GAC ACA GGC GTG TAT TAC TGT GCC TGC CGC AGT TAC GGG AGG ACC CCG TAC TAC
     D   T   G   V   Y   Y   C   A   C   R   S   Y   G   R   T   P   Y   Y
                                                                    NheI
             387 FR4         396             405             414             423
    TTT GAC TTC TGG GGC CAA GGC ACC ACT CTC ACC GTC TCC TCA GCT AGC 3'
     F   D   F   W   G   Q   G   T   T   L   T   V   S   S   A   S
```

FIGURE 16

Anti-gp39 24-31 V_K Sequence

```
   Bgl II      9              18              27              36              45              54
5' AGA TCT CTC ACC ATG GGC TTC AAG ATG GAG TCA CAG TTT CTG GCC TTT GTA TTC
   --- --- --- --- --- --- --- --- --- --- --- --- --- --- --- --- --- ---
                   M   G   F   K   M   E   S   Q   F   L   A   F   V   F 63              72              81   +1  90  FR1  99             108
   GCG TTT CTC TGG TTG TCT GGT GTT GAT GGA|GAC ATT GTG ATG ACC CAG TCT CAA
   --- --- --- --- --- --- --- --- --- ---|--- --- --- --- --- --- --- ---
    A   F   L   W   L   S   G   V   D   G | D   I   V   M   T   Q   S   Q 117             126             135             144             153| CDR1 162
   AAA TTC ATG TCC ACA TCC GTA GGA GAC AGG GTC AGC ATC ACC TGC|AAG GCC AGT
   --- --- --- --- --- --- --- --- --- --- --- --- --- --- ---|--- --- ---
    K   F   M   S   T   S   V   G   D   R   V   S   I   T   C | K   A   S 171             180             189  FR2 198             207             216
   CAG AAT GTG ATT ACT GCT GTA GCC|TGG TAT CAA CAG AAA CCA GGA CAA TCT CCT
   --- --- --- --- --- --- --- ---|--- --- --- --- --- --- --- --- --- ---
    Q   N   V   I   T   A   V   A | W   Y   Q   Q   K   P   G   Q   S   P

225            |234 CDR2 243             252| FR3 261             270
   AAA TTG CTG ATT TAC|TCG GCA TCC AAT CGG TAC ACT|GGA GTC CCT GAT CGC TTC
   --- --- --- --- ---|--- --- --- --- --- --- ---|--- --- --- --- --- ---
    K   L   L   I   Y | S   A   S   N   R   Y   T | G   V   P   D   R   F 279             288             297             306             315             324
   TCA GGC AGT GGG TCT GGG ACA GAT TTC ACT CTC ACC ATC AGC AAT ATG CAG TCT
   --- --- --- --- --- --- --- --- --- --- --- --- --- --- --- --- --- ---
    S   G   S   G   S   G   T   D   F   T   L   T   I   S   N   M   Q   S 333             342            |351 CDR3 360             369            |378
   GAA GAC CTG GCA GAT TAT TTC TGC|CAG CAA TAT AAC AGC TAT CCG TAC ACG|TTC
   --- --- --- --- --- --- --- ---|--- --- --- --- --- --- --- --- ---|---
    E   D   L   A   D   Y   F   C | Q   Q   Y   N   S   Y   P   Y   T | F

FR4 387             396             405 Bsi WI
   GGA GGG GGG ACC AAG CTG GAA ATC AAA CGT ACG 3'
   --- --- --- --- --- --- --- --- --- --- ---
    G   G   G   T   K   L   E   I   K   R   T
```

FIGURE 17

Anti gp39 24-31 V_H Sequence

```
       SalI
      ┌─────┐     9              18              27              36              45              54
5'    GTC GAC ATG ATG GTG TTA AGT CTT CTG TAC CTG TTG ACA GCC CTT CCG GGT TTC
              M   M   V   L   S   L   L   Y   L   L   T   A   L   P   G   F
                  +1
                  63      FR1  72              81              90              99             108
      CTG TCA GAG GTG CAG CTT CAG GAG TCA GGA CCT AGC CTC GTG AAA CCT TCT CAG
       L   S   E   V   Q   L   Q   E   S   G   P   S   L   V   K   P   S   Q 117             126             135             144            153 CDR1       162
      ACT CTG TCC CTC ACC TGT TCT GTC ACT GGC GAC TCC ATC ACT AAT GGT TTC TGG
       T   L   S   L   T   C   S   V   T   G   D   S   I   T   N   G   F   W

171  FR2  180             189             198            207    CDR2       216
      ATC TGG ATC CGG AAA TTC CCA GGG AAT AAA CTT GAG TAC ATG GGC TAC ATA AGT
       I   W   I   R   K   F   P   G   N   K   L   E   Y   M   G   Y   I   S
                                                                              FR3
                 225             234             243             252            261            270
      TAC AGT GGT AGC ACT TAC TAC AAT CCA TCT CTC AAG AGT CGA ATC TCC ATC ACT
       Y   S   G   S   T   Y   Y   N   P   S   L   K   S   R   I   S   I   T 279             288             297             306             315             324
      CGC GAC ACA TCC CAG AAC CAG TTC TAC CTA CAA TTG AAT TCT GTG ACT ACT GAG
       R   D   T   S   Q   N   Q   F   Y   L   Q   L   N   S   V   T   T   E 333             342             351  CDR3 360             369             378
      GAC ACA GGC ACA TAT TAC TGT GCC TGC CGC AGT TAC GGG AGG ACC CCG TAC TAC
       D   T   G   T   Y   Y   C   A   C   R   S   Y   G   R   T   P   Y   Y

387 FR4         396             405             414          423   NheI
      TTT GAC TTC TGG GGC CAA GGC ACC ACT CTC ACC GTC TCC TCA GCT AGC 3'
       F   D   F   W   G   Q   G   T   T   L   T   V   S   S   A   S
```

FIGURE 18

ANTI-CD154 ANTIBODIES HAVING IMPAIRED FCR BINDING AND/OR COMPLEMENT BINDING PROPERTIES AND RELATED THERAPIES

PRIORITY INFORMATION

Related Applications

This application is a divisional of U.S. application Ser. No. 15/074,505, filed Mar. 18, 2016, which is a divisional of U.S. application Ser. No. 13/648,808, filed Oct. 10, 2012 (now U.S. Pat. No. 9,321,833), which is a continuation in part of U.S. application Ser. No. 13/439,186 filed Apr. 4, 2012, (now U.S. Pat. No. 8,852,597), which claims priority to U.S. Provisional Application No. 61/471,287 filed Apr. 4, 2011. Each of the applications above are incorporated by reference in their entirety.

SEQUENCE LISTING

This application includes as part of its disclosure a biological sequence listing text file named "43260o0109.txt" having a size of 23,205 bytes that was created Apr. 15, 2019, which is hereby incorporated by reference in its entirety.

BACKGROUND

Field of the Invention

The present invention relates to improved anti-CD154 (CD40L) antibodies having reduced toxicity and their use in immune therapies, especially treatment of inflammatory disorders, allergy, autoimmunity, transplant, and cancers. In particular the invention provides anti-CD154 antibodies that are modified such that they do not elicit thrombogenic or clotting reactions in vivo, but which still retain desired therapeutic properties such as the induction of immune tolerance and the blockade of humoral immunity.

Description of Related Art

CD40L (CD154) is a highly validated and valuable therapeutic target in autoimmunity, graft rejection and other immune-related diseases in mice, non-human primates (NHP) and humans. In numerous Phase II Clinical Trials, α-CD154 has been shown to effectively block the activities of CD154 in vivo and ameliorate disease. αCD154 is distinct from all other therapeutics in its impact on the immune response; it is one of the only therapeutics that can induce functional immunological tolerance, as demonstrated both in mice and monkeys. In mice, virtually all autoimmune disease models can be effectively ameliorated with αCD154 therapy (Noelle, R. J., Mackey, M., Foy, T., Buhlmann, J. and Burns, C., CD40 and its ligand in autoimmunity. Ann N Y Acad Sci 1997. 815: 384-391; Mackey, M. F., Barth, R. J., Jr. and Noelle, R. J., The role of CD40/CD154 interactions in the priming, differentiation, and effector function of helper and cytotoxic T cells. J Leukoc Biol 1998. 63: 418-428; Noelle, R. J., CD40 and its ligand in cell-mediated immunity. Agents Actions Suppl 1998. 49: 17-22; and Quezada, S. A., Jarvinen, L. Z., Lind, E. F. and Noelle, R. J., CD40/CD154 Interactions at the Interface of Tolerance and Immunity. Annu Rev Immunol 2004. 22: 307-328), with long-term remission observed.

In NHP, permanent allograft tolerance can be achieved using short courses of treatments comprised of αCD154 (Kenyon, N. S., Chatzipetrou, M., Masetti, M., Ranuncoli, A., Oliveira, M., Wagner, J. L., Kirk, A. D., Harlan, D. M., Burkly, L. C. and Ricordi, C., Long-term survival and function of intrahepatic islet allografts in rhesus monkeys treated with humanized anti-CD154. Proc Natl Acad Sci USA 1999. 96: 8132-8137; Kirk, A. D., Burkly, L. C., Batty, D. S., Baumgartner, R. E., Berning, J. D., Buchanan, K., Fechner, J. H., Jr., Germond, R. L., Kampen, R. L., Patterson, N. B., Swanson, S. J., Tadaki, D. K., TenHoor, C. N., White, L., Knechtle, S. J. and Harlan, D. M., Treatment with humanized monoclonal antibody against CD154 prevents acute renal allograft rejection in nonhuman primates. Nat Med 1999. 5: 686-693).

Also, Phase II Clinical Trials in humans have indicated that αCD154 is effective in SLE (Sidiropoulos, P. I. and Boumpas, D. T., Lessons learned from anti-CD154 treatment in systemic lupus erythematosus patients. Lupus 2004. 13: 391-397), Multiple Sclerosis (see preliminary data) and idiopathic thrombocytopenia (Sidiropoulos, P. I. and Boumpas, D. T., Lessons learned from anti-CD154 treatment in systemic lupus erythematosus patients. Lupus 2004. 13: 391-39). As such, αCD154 is a unique drug that will allow for short-term intervention with long-term clinical benefit. Its failures have not been in efficacy, but due to an unanticipated toxicity.

Further, in the early 1990's IDEC Pharmaceuticals and Biogen Inc. (now Biogen Idec) launched two different αCD154 mAbs into multiple Phase I/II Clinical Trials. The antibody developed by IDEC (IDEC-131) was derived from a murine anti-hCD154 developed at Dartmouth College.

This antibody and humanized variants are disclosed in U.S. Pat. No. 6,440,418 the contents of which are incorporated by reference herein. While early indications demonstrated that the drug was highly effective, toxicity of the αCD154 prohibited continued clinical development. In the trials, the observed toxicity included the induction of thromboembolic events in patients. Based on toxicity concerns, all trials were suspended and efforts were directed towards re-engineering the mAbs to sustain efficacy and reduce toxicity. While reduced toxicity has been achieved, there has been a substantial decrease in efficacy and the tolerance-inducing capacity of αCD154 mAbs (Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., The contribution of Fc effector mechanisms in the efficacy of anti-CD154 immunotherapy depends on the nature of the immune challenge. Int Immunol 2004. 16: 1583-1594). None of the engineered mAb forms have progressed significantly into the clinic due to loss in efficacy.

Recently, Biogen-Idec and UCB entered into a collaboration relating to the study of anti-CD40L antibodies (see, http://www.news-medical.net/news/20111219/ALS-TDI-Biogen-Idec-and-UCB-enter-agreement-to-study-anti-CD40L-antibody-for-ALS.aspx). This study relates to a Pegylated Fab of an αCD154.

Notwithstanding the foregoing, there is still a significant need in the art for improved anti-CD154 antibodies, i.e., those which are both safe and effective. This invention attains these goals.

DETAILED DESCRIPTION OF THE FIGURES

FIG. 1 shows the impact of anti-CD154 therapy on relapse rate in RR MS Patients. Patients with active disease were recruited into trial and were treated with 4 escalating doses of IDEC-131 every week. Following treatment all patients were followed by EDSS scoring as well as assessment of gadolinium-enhanced lesions.

FIG. 2 shows the nucleotide sequence of a hamster anti-murine CD154. Shown are the k and heavy chain sequence for the MR1 anti-human CD40L (CD154) hamster IgG1.

FIG. 3 shows the reduction in FcR binding in the E223PIgG1 MR1 IgG1 variant.

FIG. 4 shows the effects of mutations in MR1 that ablate C1q binding.

FIG. 5 shows that the loss of complement activation does not reduce the ability of anti-CD154 to induce tolerance.

FIG. 6 shows the thrombotic stress signs in all tested animals arranged by treatment groups.

FIG. 7 shows platelet counts of all animals used in the study, arranged by treatment groups.

FIG. 8: Average number of clots per field (200× original magnification) as observed microscopically, arranged by treatment groups.

FIG. 9: Sample images of H&E stained lung sections from animals injected with PBS. Header values indicate original microscopic magnification. With these example images and with those below, the higher magnification images were acquired from within the field of the first (100×) image.

FIG. 10: Sample images of H&E stained lung sections from animals injected with MR1-WT. Header values indicate original microscopic magnification. Blue arrow identifies thrombus.

FIG. 11: Sample images of H&E stained lung sections from animals injected with N325L. Header values indicate original microscopic magnification FIG. 12: Sample images of H&E stained lung sections from animals injected with K326V. Header values indicate original microscopic magnification FIG. 13: Sample images of H&E stained lung sections from animals injected with E269R. Header values indicate original microscopic magnification.

FIGS. 14-16 contain humanized sequences corresponding to an anti-human CD154 antibody (IDEC-131).

FIGS. 17 and 18 contain the variable sequences for the parent chimeric antibody from which IDEC-131 was derived.

DETAILED DESCRIPTION

Prior to disclosing the invention in detail the following definitions are provided. Unless defined otherwise, all technical and scientific terms used herein have the same meaning as commonly understood to one of ordinary skill in the art to which this invention belongs.

As used herein, oligonucleotide sequences that are complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to" refers to the binding, duplexing or hybridizing of a molecule substantially to or only to a particular nucleotide sequence or sequences under stringent conditions when that sequence is present in a complex mixture (e.g., total cellular) DNA or RNA.

"Mutation or mutations that eliminate or reduces FcR binding and which eliminates toxicity" herein refers to a mutation or mutations that eliminate or reduce thrombocytopenia or thrombosis or clotting in vivo. The efficacy of such mutations in eliminating or reducing thrombocytopenia or thrombosis or clotting is shown infra murine thrombosis model, e.g., a mouse that has been engineered to express human FcR, and wherein said mouse is administered a chimeric antibody specific to a host compatible, i.e., anti-rodent CD40L, e.g., mouse CD40L, and which chimeric antibody contains either human IgG1 or IgG3 constant regions, and further wherein the Fc region thereof has been mutated at one or more sites to eliminate or substantially inhibit FcR binding. Exemplary sites which may be modified and specific mutations are identified in Tables 2-4 and the examples infra.

"Mutation or mutations that eliminate or reduce complement function and which maintain tolerance inducing properties" refers to mutation or mutations in human, chimeric, or humanized antibodies containing human constant regions, preferably human IgG1 or IgG3 constant regions, wherein the Fc region thereof has been mutated at one or more sites in order to eliminate or substantially reduce complement binding. Preferably such mutations will not appreciably affect the ability of the antibody to induce tolerance in vivo. This may be established using appropriate tolerance models such as the skin transplant model disclosed herein. Exemplary sites which may be modified and specific mutations are identified in Tables 2-4 and the examples infra.

A "patient" can mean either a human or non-human animal, preferably a mammal. In preferred embodiments this invention produces anti-human CD40L antibodies suitable for human therapy containing mutated IgG1 or IgG3 constant regions, wherein such mutations eliminate or substantially inhibit toxicity concerns such as thrombocytopenia or thrombosis or clotting reactions or toxicity associated with complement reactions and preferably wherein such antibodies retain the ability to induce tolerance or humoral suppression in vivo.

As used herein, "subject", as refers to an organism or to a cell sample, tissue sample or organ sample derived therefrom, including, for example, cultured cell lines, biopsy, blood sample, or fluid sample containing a cell. In many instances, the subject or sample derived therefrom, comprises a plurality of cell types. In one embodiment, the sample includes, for example, a mixture of tumor and normal cells. In one embodiment, the sample comprises at least 10%, 15%, 20%, et seq., 90%, or 95% tumor cells. The organism may be an animal, including but not limited to, an animal, such as a cow, a pig, a mouse, a rat, a chicken, a cat, a dog, etc., and is usually a mammal, such as a human.

The term "treating" in its various grammatical forms in relation to the present invention refers to preventing (i.e. chemoprevention), curing, reversing, attenuating, alleviating, minimizing, suppressing, or halting the deleterious effects of a disease state, disease progression, disease causative agent (e.g. bacteria or viruses), or other abnormal condition. For example, treatment may involve alleviating a symptom (i.e., not necessarily all the symptoms) of a disease of attenuating the progression of a disease.

"Treatment of autoimmunity" or "treating" another disease condition such as cancer, infection, allergy, transplant, graft versus host disease and other conditions wherein anti-CD154 antibodies are potentially of therapeutic benefit as used herein, refers to partially or totally inhibiting, delaying, or preventing the progression of the disease. In the case of cancer this means treating or inhibiting cancer metastasis; inhibiting, delaying, or preventing the recurrence of cancer including cancer metastasis; or preventing the onset or development of cancer (chemoprevention) in a mammal, for example, a human. In addition, the methods of the present invention may be practiced for the treatment of human patients with cancer. However, it is also likely that the methods would also be effective in the treatment of cancer in other mammals. In the preferred embodiments the subject antibodies are used to treat autoimmunity, allergy, inflammation, transplant, GVHD, bone marrow transplant (BMT), and to induce antigen specific tolerance in subjects in need thereof. Preferred indications are multiple sclerosis, lupus, ITP, IBD, Crohn's disease, psoriasis, uveitis, rheumatoid arthritis, asthma, GVHD, bone marrow transplant, oophoritis and thyroiditis.

As used herein, the term "therapeutically effective amount" is intended to qualify the amount of the treatment in a therapeutic regiment necessary to treat a condition e.g., autoimmunity.

The present invention provides novel and improved anti-CD154 antibodies for use in therapies containing mutated Fc regions that are safe and effective. These antibodies exhibit improved safety and efficacy compared to currently available anti-CD154 antibodies because of mutations that inhibit or prevent FcR binding and/or complement binding and activation.

In especially preferred embodiments the subject anti-CD154 antibodies will comprise the same CDR's as IDEC 131 and more specifically contain the humanized variable heavy and light regions of IDEC-131 or will contain a humanized variable light region and a variable heavy chain region that is at least 95%, 98% or which is identical to at least one of the humanized variable light and variable heavy sequences identified as (1), (2), (3) and (4) set forth below.

In these variable heavy and light amino acid sequences which are set forth below, the FR and CDR regions are separated by spaces and the sequences are organized as in normal antibody variable regions, i.e.: FR1 CDR1 FR2 CDR2 FR3 CDR3 FR4.

For example, in variable light sequence sequence (1) the CDRs of the variable light chain are KASQNVITAVA (CDR1), SASNRYT (CDR2) and QQYNSYPYT (CDR3) and the CDRs of the heavy chain sequence (1) are respectively NGFWI (CDR1), YISYSGSTYYNPSLKS (CDR2) and RSYGRTPYYFDF (CDR3). In preferred embodiments the anti-CD154 antibody will contain a variable light and a variable heavy sequence identical to one of those identified as variable light and variable heavy sequences (1) and (2) (any combination thereof) and the Fc region of the humanized anti-CD154 antibody will comprise mutations in the Fc region, e.g., a human IgG1 or IgG3 constant region, that preclude one or both of FcR binding and complement binding, and will be safe (not elicit thrombogenic or clotting reaction) and will induce immune tolerance or suppression of humoral immunity in vivo.

The preferred humanized variable light sequences (1), (2) (3) and (4) are forth below:

```
(1) DIVMTQSPSFLSASVGDRVTITC KASQNVITAVA
WYQQKPGKSPKLLIY SASNRYT
```

```
-continued
GVPDRFSGSGSGTDFTLTISSLQPEDFADYFC QQYNSYPYT
FGGGTKLEIK;

(2) DIVMTQSPDSLAVSLGERATINC KASQNVITAVA
WYQQKPGQSPKLLIY SASNRYT
GVPDRFSGSGSGTDFTLTISSLQAEDVADYFC QQYNSYPYT
FGGGTKLEIK;

(3) DIVMTQSPSFMSTSVGDRVTITC KASQNVITAVA
WYQQKPGKSPKLLIY SASNRYT
GVPDRFSGSGSGTDFTLTISSMQPEDFADYFC QQYNSYPYT
FGGGTKLEIK;

(4) DIVMTQSPDSMATSLGERVTINC KASQNVITAVA
WYQQKPGQSPKLLIY SASNRYT
GVPDRFSGSGSGTDFTLTISSMQAEDVADYFC QQYNSYPYT.
FGGGTKLEIK,
```

The preferred humanized variable heavy sequences (1), (2) (3) and (4) are forth below:

```
(1) EVQLQESGPGLVKPSETLSLTCTVSGDSIT NGFWI
WIRKPPGNKLEYMG YISYSGSTYYNPSLKS
RISISRDTSKNQFSLKLSSVTAADTGVYYCAC
RSYGRTPYYFDF WGQGTTLTVSS;

(2) EVQLQESGPGLVKPSQTLSLTCTVSGDSIT NGFWI
WIRKHPGNKLEYMG YISYSGSTYYNPSLKS
RISISRDTSKNQFSLKLSSVTAADTGVYYCAC
RSYGRTPYYFDF WGQGTTLTVSS;

(3) EVQLQESGPGLVKPSQTLSLTCAVSGDSIT NGFWI
WIRKHPGNKLEYMG YISYSGSTYYNPSLKS
RISISRDTSNNQFSLNLNSVTRADTGVYYCAC RSYGRTPYYFDF
WGQGTTLTVSS;

(4) EVQLQESGPGLVKPSETLSLTCAVYGDSIT NGFWI
WIRKPPGNKLEYMG YISYSGSTYYNPSLKS
RISISRDTSKNQFYLKLSSVTAADTGVYYCAC RSYGRTPYYFDF
WGQGTTLTVSS.
```

As discussed, the subject antibodies preferably will be mutated to inhibit or prevent complement binding and complement activation as well as mutations that preclude or which substantially inhibit FcR binding. This mutation was not anticipated to be beneficial to an anti-CD154 antibody to be used as a therapeutic, as prior to this invention it was thought that the therapeutic efficacy of an αCD154, aside from its ability to simply block CD154, also required complement binding. It was thought by experts that complement binding was critical for CD154 antibodies to actively induce tolerance. Also, prior to this invention it was uncertain as to whether the ability of the αCD154 antibody to bind FcR would potentially adversely affect therapeutic functionality, i.e., the antibody's ability to induce tolerance.

Notwithstanding the foregoing, the inventor proposed to develop mutated anti-CD154 antibodies that do not bind FcR and/or complement with the hope that such antibodies would maintain the full tolerance-inducing capacity of αCD154, while eliminating its toxicity. Such an antibody will realize the full potential of this extraordinary target and prove to be an invaluable therapeutic agent for the treatment of an extremely broad spectrum of immune-related diseases wherein compounds that antagonize CD40L/CD40 signaling may be used to intervene in the disease process.

That such antibodies would induce tolerance was not anticipated from prior research. For example, previous studies in NHP using aglycosylated αCD154 (αCD154$^{agly}$) antibodies that do not effectively bind complement or FcR have suggested that while the toxicities associated with αCD154 may have been eliminated, that such antibodies unfortunately eliminate the ability of the antibody to induce tolerance (Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., The contribution of Fc effector mechanisms in the efficacy of anti-CD154 immunotherapy depends on the nature of the immune challenge. Int Immunol 2004. 16: 1583-1594). This impairment of functionality (tolerance induction) would suggest that complement binding and activation is essential or at least important as to the ability of αCD154 to induce tolerance.

The prior studies which implicated complement binding to the efficacy of an αCD154 antibody, and especially its ability to be therapeutically effective such as inhibit the effects of CD154 in vivo, including especially the ability of the antibody to induce tolerance were effected in complement deficient mice. While these studies and underlying conclusions were deemed valid by other scientists, the subject inventor wanted to validate these studies in a different model because of the fact that complement deficient mice may not be the best model to study the potential therapeutic efficacy of such antibodies. In particular, it was theorized that this may not be the best model as these mice, because of their complement deficiency are defective in many aspects of immunity and also may express antibodies abnormally relative to wild-type animals, i.e., they may express grossly altered antibodies such as antibodies having aberrant or absent glycosylation (aglycosylated). Based on the potential effects of these abnormalities on the induction of tolerance in vivo, the present inventor hypothesized that the prior studies did not convincingly determine whether complement binding is indeed essential to the ability of an anti-CD40L antibody to induce tolerance, notwithstanding the conclusions of reputable scientists involved in these studies.

More particularly, it was theorized that the reported results as to the involvement of complement in tolerance may be erroneous or overstated. Therefore, in order to critically assess the effects of complement binding/activation and FcR binding on therapeutic efficacy and toxicity the inventor elected to construct anti-CD154 antibodies containing mutations in their Fc region that preclude or prevent complement binding and/or FcR binding. It was theorized that the toxicity of an anti-CD154 containing a human constant region which results in thrombosis may be addressed by introducing mutations which eliminate FcR binding, and potentially that introducing such changes may not impact therapeutic efficacy such as the ability of the mutated antibody to induce tolerance, inhibit humoral and/or cellular immunity and to inhibit other activities elicited by CD154 and CD154/CD40 binding interactions.

In order to achieve these objectives the inventor desired to effect these studies in an appropriate animal model. To meet these objectives the inventor, elected to conduct experiments in a rodent animal model for assaying thrombocytopenia and thrombosis which comprises and expresses human FcRs. This animal model is disclosed in more detail in the experimental examples infra.

As disclosed infra, the results of these experiments confirmed the inventor's hope, i.e., that anti-CD154 antibodies containing human constant regions such as IgG1 or IgG3 may be mutagenized at specific sites in their Fc regions in order to eliminate one or both of FcR binding and/or complement binding to eliminate toxicity (thrombosis, clotting reactions), potentially the without loss of functionality.

Accordingly, based on the foregoing, mutated versions of antibodies containing mutated human constant regions, i.e., mutant IgG1 (($\gamma_1$, $\gamma_1^{-C}$, $\gamma_1^{-FcR}$, $\gamma_1^{-C/FcR}$) which are specific to CD154 and containing mutations that disrupt complement binding and/or FcR binding are disclosed herein.

In the working examples specific mutants were tested in order to assess whether efficacy and toxicity of αCD154 are dependent on complement binding (K322A, P331G, P331G/K322A) or FcR binding (N325L, K326V, E269R). Each of the complement binding engineered forms of αCD154 was tested for its ability to induce tolerance and the FcR binding mutants for their propensity to induce thromboembolic events in murine models.

While these specific mutations were exemplified, based on the results disclosed infra it is anticipated that other recombinant anti-CD154 antibodies may be developed comprising other Fc mutations reported to disrupt complement binding and/or FcR binding with similar properties, i.e./no toxicity and/or retained efficacy, including the ability to elicit tolerance in vivo. As discussed herein, other sites in the Fc region of human IgG1 and other human constant regions are known to be involved in complement binding and/or activation as well as FcR binding. Accordingly, the described mutations are exemplary of appropriate mutations in the Fc region of IgG1 or IgG3 or other antibodies that result in loss of one or both of complement binding and FcR binding.

As further discussed in the examples, the tolerance inducing effects of the complement-binding mutant αCD154 variants were evaluated in a well-studied model of haplomismatched skin allograft survival, where long-term tolerance is induced by the administration of αCD154 and alloantigen. However, other tolerance models may alternatively be used to assess the ability of a αCD154 complement deficient and/orFcR deficient variant (containing a mutated Fc region) to induce tolerance.

The thromboembolic activities of the FcR mutated αCD154 is tested in a murine model expressing the human FcαRIIA receptor that reproduces the events observed in NHP (Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., The contribution of Fc effector mechanisms in the efficacy of anti-CD154 immunotherapy depends on the nature of the immune challenge. Int Immunol 2004. 16: 1583-1594). In such mice, treatment with αCD154 (anti-mouse CD154) induces pulmonary thrombi; therefore we evaluated therein whether the loss of FcR binding in anti-mouse CD154 antibodies containing mutated human Fc regions (mutated IgG1 constant regions) eliminates or appreciably reduces the formation of thrombi. Thereby, the inventor can introduce specific Fc mutations, and based on the effects of such antibodies containing these Fc mutations identify specific mutations that result in the eradication of the toxicity associated with αCD154 therapy. Thereupon, human, humanized or chimeric anti-human CD154 antibodies, which elicit no toxicity but which retain efficacy, may be produced containing such mutated human Fc regions.

As shown by the results in the experimental examples infra, the present inventor has surprisingly shown, in contrast to the prior scientific consensus that complement binding is not required for the ability of an αCD154 to induce T cell tolerance. Also, the results indicate that some, but not all mutations that reportedly impact FcR binding, eliminate the thromboembolic effects of αCD154. Based thereon, the invention provides a means for selecting antibodies containing appropriate Fc mutations that eliminate complement binding and/or FcR binding and which are well suited for use in anti-CD154 therapies such as described herein and which are not toxic.

In this regard, aside from the toxicity associated with FcR binding, because the subject antibodies may be mutated to eliminate complement binding, the subject recombinant anti-CD154 antibodies are further believed to be less subject to toxicity concerns. This is advantageous because it has been reported that complement binding by some therapeutic antibodies may result in undesired toxicity in vivo. Accordingly, the invention provides improved therapeutic anti-CD154 antibodies that should exhibit improved safety in human patients both from an elimination of thrombolytic adverse events attributable to FcR binding and further by a reduction or elimination of complement associated toxicity. (See, e.g., "Complement Activation Plays a Key Role in Antibody-Induced Infusion Toxicity in Monkeys and Rats", The Journal of Immunology Feb. 15, 2008 vol. 180 no. 4 2294-2298).

The mutated CD154 specific antibodies of the present invention having altered complement and/or FcR binding may be used for the treatment and prevention of any condition wherein antagonizing the effects of CD154 may be therapeutically effective, and may reduce the symptoms of the disease. Examples thereof include the treatment of allergic, autoimmune, cancer, transplant, GVHD, inflammatory and other conditions, especially conditions wherein the induction of tolerance and/or the suppression of humoral immunity is therapeutically desirable. Specific examples are listed in Table 1.

TABLE 1

Diseases and species that demonstrate efficacy of αCD154.

| | |
|---|---|
| Multiple sclerosis (EAE) | Mouse, Human |
| Rheumatoid arthritis | Mouse |
| Inflammatory bowel disease | Mouse |
| Thyroiditis | Mouse |
| Systemic Lupus Erythematosis | Mouse, Human |
| Autoimmune thrombocytopenia | Human |
| Diabetes | Mouse |
| Graft vs. host disease | Mouse |
| Kidney transplantation | Monkey |
| Skin transplantation | Mouse, Monkey |
| BM transplantation | Mouse |
| Atherosclerosis | Mouse |

The subject antibodies which target CD154, and which possess improved safety properties, are of great therapeutic potential as CD154 is an extremely attractive target for immune intervention in a wide spectrum of autoimmune, and graft-related diseases. Virtually all models of autoimmune disease in mice (see Table 1) are therapeutically ameliorated by αCD154 treatment. Furthermore, the efficacy in mouse models has translated extremely well into man, as treatment of MS, Lupus and ITP all have documented efficacy of ahuman CD154 in clinical trials.

Beyond simply blocking CD154-CD40 interactions, αCD154 therapy leads to the induction of immunologic tolerance (Prevention of transplant rejection by blocking CD40-CD154 interactions has been repeatedly documented for the induction of long-term tolerance to skin, Gordon, E. J., Markees, T. G., Phillips, N. E., Noelle, R. J., Shultz, L. D., Mordes, J. P., Rossini, A. A. and Greiner, D. L., Prolonged survival of rat islet and skin xenografts in mice treated with donor splenocytes and anti-CD154 monoclonal antibody. Diabetes 1998. 47: 1199-1206.; Markees, T. G., Phillips, N. E., Noelle, R. J., Shultz, L. D., Mordes, J. P., Greiner, D. L. and Rossini, A. A., Prolonged survival of mouse skin allografts in recipients treated with donor splenocytes and antibody to CD40 ligand. Transplantation 1997. 64: 329-335; Jarvinen, L. Z., Blazar, B. R., Adeyi, O. A., Strom, T. B. and Noelle, R. J., CD154 on the surface of CD4+CD25+ regulatory T cells contributes to skin transplant tolerance. Transplantation 2003. 76: 1375-1379; Quezada, S. A., Fuller, B., Jarvinen, L. Z., Gonzalez, M., Blazar, B. R., Rudensky, A. Y., Strom, T. B. and Noelle, R. J., Mechanisms of donor-specific transfusion tolerance: pre-emptive induction of clonal T-cell exhaustion via indirect presentation. Blood 2003. 102: 1920-1926; Frleta, D., Lin, J. T., Quezada, S. A., Wade, T. K., Barth, R. J., Noelle, R. J. and Wade, W. F., Distinctive maturation of in vitro versus in vivo anti-CD40 mAb-matured dendritic cells in mice. J Immunother 2003. 26: 72-84; Quezada, S., Eckert, M., Schned, A., Noelle, R. J. and Burns, C., Distinct mechanisms of action of anti-CD154 in early versus late treatment of murine lupus nephritis. Arth Rheum. 2003.; Elster, E. A., Xu, H., Tadaki, D. K., Montgomery, S., Burkly, L. C., Berning, J. D., Baumgartner, R. E., Cruzata, F., Marx, R., Harlan, D. M. and Kirk, A. D., Treatment with the humanized CD154-specific monoclonal antibody, hu5C8, prevents acute rejection of primary skin allografts in nonhuman primates, Transplantation 2001. 72: 1473-1478., islets (Benda, B., Ljunggren, H. G., Peach, R., Sandberg, J. O. and Korsgren, O., Co-stimulatory molecules in islet xenotransplantation: CTLA4Ig treatment in CD40 ligand-deficient mice. Cell transplantation 2002. 11: 715-720) bone marrow (Wekerle, T. and Sykes, M., Mixed chimerism and transplantation tolerance. Annual review of medicine 2001. 52: 353-370[19], and a myriad of other transplanted organs (Camirand, G., Caron, N. J., Turgeon, N. A., Rossini, A. A. and Tremblay, J. P., Treatment with anti-CD154 antibody and donor-specific transfusion prevents acute rejection of myoblast transplantation. Transplantation 2002. 73: 453-461; Tung, T. H., Mackinnon, S. E. and Mohanakumar, T., Long-term limb allograft survival using anti-CD154 antibody in a murine model. Transplantation 2003. 75: 644-650). Furthermore, ahuman CD154 in NHP has been shown to induce long-term tolerance to allogeneic skin transplants.

Whereas anti-CD154 antibodies have been reported to have significant therapeutic potential, the development of the inventive antibodies containing mutated Fc regions for use as therapeutics was not suggested by the prior art as prior to the present invention it was thought that C' was involved (required) for mediating graft tolerance. More specifically it was thought that αCD154 must accomplish two things to induce tolerance, prevent inflammation and activate C'. Surprisingly, this is not the case.

Quite surprisingly we teach herein that neither C' activating activity, nor binding to FcR is necessary for an anti-CD154 antibody to be therapeutically effective (induce tolerance) and that antibodies which comprise specific mutations that eliminate or reduce FcR binding do not elicit thrombolytic or thrombocytopenia and therefore should be effective and safe.

This was theorized in part because previous aglycosylated antibodies that have resulted in complete disabling of the Fc region of anti-CD154 have eradicated toxicity, but substantially inhibited tolerance inducing efficacy. Only extremely high levels in mice (50 mg/kg×3) of Fc disabled anti-CD154 were shown to induce tolerance, but lower doses (20 mg/kg) in monkeys could not induce tolerance.

By contrast, the inventor theorizes based on the results herein that C' activating activity is not required for the ability to induce tolerance and further theorize that binding to FcR may not be required for an anti-CD154 antibody to be therapeutically effective, and specifically to induce tolerance or humoral suppression. Based on the foregoing, and the results reported in the examples infra, the inventive anti-CD154 antibodies which comprise specific mutations that eliminate or reduce FcR binding and which do not elicit thrombolytic or thrombocytopenia and/or which further contain mutations in the Fc region that eliminate or reduce complement binding should be effective and moreover, substantially more safe than prior reported anti-CD154 antibodies, developed as potential human antibody therapeutics. In fact, to date, no anti-CD154 antibody has been approved for human therapy notwithstanding the fact that the potential use of antibodies that target CD154 was reported in the mid-90's and several such antibodies were in clinical development.

Assessing αCD154 Toxicity in Mice

Earlier studies clearly documented the thrombogenic activities of anti-CD154 mAbs in cynomolgus monkeys. In evaluating engineered forms of anti-CD154 mAbs, studies in NHP is a costly and cumbersome approach. Therefore, less cumbersome and costly methods would be desirable such as assays using transgenic rodents.

It is believed that the binding of anti-C154-sCD154 (soluble (s) CD154 is present in serum) immune complexes (IC) to platelets may be the basis for the thrombogenic activity of anti-CD154 mAbs. Studies have shown that anti-CD154 IC activate platelets in vitro via the IgG receptor (human FcγRIIA) (Langer, F., Ingersoll, S. B., Amirkhosravi, A., Meyer, T., Siddiqui, F. A., Ahmad, S., Walker, J. M., Amaya, M., Desai, H. and Francis, J. L., The role of CD40 in CD40L- and antibody-mediated platelet activation. Thrombosis and homeostasis 2005. 93: 1137-1146) on platelets and could cause thrombi formation. The prothrombotic effects of anti-CD154 (using a human IgG1 variant of MR1) also have been evaluated in vivo using hFcγRIIA transgenic mice (Robles-Carrillo, L., Meyer, T., Hatfield, M., Desai, H., Davila, M., Langer, F., Amaya, M., Garber, E., Francis, J. L., Hsu, Y. M. and Amirkhosravi, A., Anti-CD40L immune complexes potently activate platelets in vitro and cause thrombosis in FCGR2A transgenic mice. J Immunol 2010. 185: 1577-1583). These mice were produced because mice do not express FcγRIIA on platelets. Upon injection of hIgG1/D154-sCD154 IC, mice developed pulmonary thrombi consisting of platelet aggregates and fibrin, similar to that observed in NHP treated with glycosylated anti-CD154 antibodies. By contrast, the administration of aglycosylated anti-CD154 (hIgG1MR1agly) did not induce pulmonary thrombi. The inventor accordingly elected to use this in vivo rodent assay to test the prothrombotic activity of different engineered human $IgG_1$ αCD154.

Therapeutic Applications of CD154 Antibodies of the Invention

As a category, there are nearly 50 million people in the US suffering from the 100+ known autoimmune diseases. Treatment costs are estimated to be over $100B/year and that figure is likely an underestimate. Costs for the 7 major autoimmune diseases (IBD, Lupus, MS, RA, psoriasis and scleroderma) alone are estimated to range between $51-70.6B/yr. In 2008, there were 23, 288 transplants performed in the US. With an average cost of $22, 350/yr, over $500M/yr is spent on immunosuppression post-transplant.

αCD154 is potentially one of the most therapeutically valuable drugs for the treatment of autoimmunity and graft rejection. In addition to the demonstrated clinical efficacy seen in Lupus and ITP, the inventor was involved in a completed a Phase I Clinical Trial in remitting/relapsing (RR) MS. While only a small cohort of patients was treated (12), the results of the trial were striking. The conclusions of the trial were that 4 weekly treatments with IDEC-131 resulted in: 1) No significant changes in EDSS from baseline to 5 years for all doses; 2) Improved EDSS correlated with increased dose and 3) Long-term follow up demonstrated a profound reduction in clinical relapse rate that compares favorably to current IMD. As a result of this trial, we were awarded an NIH grant to execute a Phase II Clinical Trial in R/R MS but due to toxicity associated with αCD154 seen in other trials, the αCD154 became unavailable.

We theorized that if this toxicity problem can be resolved, and efficacy sustained, that αCD154 is a viable and attractive therapeutic that should be permitted to re-enter human Trials. The subject improved anti-CD154 antibodies may be used in any indication where intervention or blocking of the CD154 binding interaction is therapeutically desirable. These conditions include inflammatory, autoimmune, allergic, cancer, transplant, infectious, GVHD and other indications. The present inventor will initially focus on developing anti-CD154 Abs for treating MS and for commercial development as this is a devastating condition that affects many individuals, including many women in their late 20's and 30's.

There is a wealth of data indicating that complement activation is critical for the induction of tolerance by αCD154. Studies in complement deficient mice clearly show that αCD154 is completely ineffective at inducing tolerance. While this has been interpreted as resulting from complement-mediated elimination of activated T cells, the results contained in this application show that this is incorrect. Indeed, the present inventor initially thought that C' activation at the cell surface by αCD154 facilitates the generation of adaptive $r^eg$ and explained why aglycosylated αCD154 mAbs in NHP are ineffective at inducing tolerance. However, this invention reveals that to be erroneous as cannot be true as we teach herein the production of αCD154 mabs that do not bind C1q and yet still effectively induce tolerance. It is anticipated that such antibodies will be safe and effective and that these αCD154 mAbs useful for immune intervention.

Engineering Safe, Tolerance-Inducing αCD154.

To demonstrate efficacy and toxicity, a model antibody, MR1, was chimerized and engineered to eliminate or reduce complement binding (K322A, P331G, P331G/K322A) or FcR binding (N325L, K326V, E269R). Studies have shown that the human IgG1 version of MR1 is thrombogenic (Robles-Carrillo, L., Meyer, T., Hatfield, M., Desai, H., Davila, M., Langer, F., Amaya, M., Garber, E., Francis, J. L., Hsu, Y. M. and Amirkhosravi, A., Anti-CD154 immune complexes potently activate platelets in vitro and cause thrombosis in FCGR2A transgenic mice. J Immunol 2010. 185: 1577-1583) and that it can induce tolerance (Daley, S. R., Cobbold, S. P. and Waldmann, H., Fc-disabled anti-mouse CD40L antibodies retain efficacy in promoting transplantation tolerance. Am J Transplant 2008. 8: 2265-2271).

We teach herein the synthesis of a chimeric hIgG1 form of MR1, which is engineered to contain well known mutations in the hIgG1 Fc region reported to disrupt C1q binding or FcR binding. If this is shown to be safe and effective, i.e., eliminate thrombotic properties while maintaining tolerogenic properties this demonstrates that other anti-CD154 antibodies, particularly those that bind human CD154 may be synthesized by engineering similar mutations that eliminate FcR binding and optionally complement binding, which eliminate or reduce thrombosis or thrombocytopenia, while maintaining the antibody's ability to induce tolerance.

As disclosed in the working examples, the first step in engineering the hamster amurine CD154 into a human IgG1 is to clone and sequence the κ and γ heavy chains. This has been accomplished and is presented in FIG. 2.

The generation and characterization of a series of Fc and C' variants of the hIgG1 form of MR1 is then performed. Mutagenesis of residue 322 from K→A (K322A) of IgG1 has been shown to abrogate complement activation. It has been shown that this variant binds human complement C1q with greatly lowered affinity and to inefficiently activate human C'(Hessell, A. J., Hangartner, L., Hunter, M., Havenith, C. E., Beurskens, F. J., Bakker, J. M., Lanigan, C. M., Landucci, G., Forthal, D. N., Parren, P. W., Marx, P. A. and Burton, D. R., Fc receptor but not complement binding is important in antibody protection against HIV. Nature 2007. 449: 101-104).

In addition the antibody was engineered in an effort to eliminate or reduce FcR binding in a manner that eliminates thrombotic or clotting toxic reactions in vivo while not impacting its desired effects on immunity such as tolerance.

In this regard, there are sites reported to eliminate or reduce FcR binding. However, their effects on functionality (tolerance) and toxicity (thrombosis) of anti-CD154 antibodies were uncertain.

For example, Shields R L, Namenuk A K, Hong K, et al. (High resolution mapping of the binding site on Human IgG1 for Fc for FcγRI, Fc for FcγRII, Fc for FcγRIII, and FcRn) report the design of IgG1 variants with impaired binding to the Fc for FcγR. J BiolChem 2001; 276: 6591-604) In addition, some patents (US20070237767 and US20100104564) describe Fc mutagenesis to eliminate FcR binding.

Exemplary mutations reported to significantly reduce FcR binding are summarized in Table 2, 3 and 4 below. Table 4 also identifies mutations that affect complement binding. Reported activities are reported as relative folds comparing to the wild type Fc.

TABLE 2

Shields' 2001 paper

| Fc mutation | FcγRI | FcγRIIa | FcγRIIb | FcγRIIIa | FcRn |
|---|---|---|---|---|---|
| E233P | 0.12 | 0.08 | 0.12 | 0.04 | 0.54 |
| D265A | 0.16 | 0.07 | 0.13 | 0.09 | 1.23 |
| D265N |  | 0.02 | 0.03 | 0.02 |  |
| D270N |  | 0.03 | 0.05 | 0.04 |  |
| N297A | 0.15 | 0.05 | 0.1 | 0.03 | 0.8 |
| S298N |  | 0.05 | 0.08 | 0.06 |  |
| P329A | 0.48 | 0.08 | 0.12 | 0.21 | 0.8 |
| D270A | 0.76 | 0.06 | 0.1 | 0.14 | 1.05 |

TABLE 3

US20100104564

| Fc mutation | FcγRI | FcγRIIa (H131) | FcγRIIa (R131) | FcγRIIb | FcγRIIIa (V158) | FcγIIIa (F158) |
|---|---|---|---|---|---|---|
| K326V | 0.52 | 0.01 | 0.01 | 0.02 | 0.87 | 2.34 |
| V369R | 0.79 | 0.01 | 0.02 | 0.03 | 0.93 | 1.64 |
| F405K | 1.52 | 0.02 | 0.02 | 0.02 | 1.08 | 2.55 |
| L410P | 1.27 | 0.01 | 0.01 | 0.01 | 0.99 | 1.75 |
| V427R | 1.69 | 0.03 | 0.05 | 0.03 | 1.27 | 0.59 |

TABLE 4

US20070237767

| Variant # | Fc mutation | FcγRI | FcγRIIa | FcγRIIb | FcγRIIc | FcγRIIIa | C1q | FcRn |
|---|---|---|---|---|---|---|---|---|
| 113 | L234N | 0.1 | 0.19 | 2.05 |  | 0.49 | 1.18 | 1.06 |
| 744 | G237M | 0.07 | 0.14 | 0.57 | 0.66 | 0.1 | 1.8 | 1.74 |
| 88 | S239F | 0.28 | 0.02 | 0.33 |  | 0.1 | 0.95 | 0.85 |
| 826 | V262E | 1.03 | 0.16 | 0.92 | 36.47 |  | 2.85 | 9.27 |
| 76 | V264F | 0.43 | 0.05 | 0.22 |  | 0.06 | 1.87 | 1.07 |
| 143 | V266T | 0.28 | 0.1 | 0.16 | 0.18 |  | 1.21 | 0.53 |
| 228 | S267N | 0.72 | 0.08 |  |  | 0.27 | 3.18 | 0.85 |
| 148 | E269R | 0.07 | 0.07 | 0.13 | 0.06 | 0.05 | 1.15 | 0.72 |
| 779 | N286E |  | 0.07 | 0.38 | 0.37 | 0.01 | 0 | 2.12 |
| 858 | N297R | 0.01 | 0.01 | 0.01 | 0.06 | 0.01 |  | 0.45 |
| 80 | T299A | 0.01 | 0.1 | 0.56 | 72.84 | 0.06 | 2.31 | 0.82 |
| 870 | R301D | 0.87 | 0.11 | 0.06 | 0.04 | 0.03 | 1.58 | 0.5 |
| 84 | N325L | 0.42 | 0.04 | 1.46 |  | 0.03 | 2.18 | 0.91 |
| 161 | N325E | 1.34 | 0.09 | 0.05 | 0.03 | <0.02 | 0.86 | 0.55 |
| 473 | L328R | 0.07 | 0.1 | 0.88 | 0.37 | 0.11 | 1.21 | 1.82 |

General Description of Inventive Methods

Preparation of MR1 Variants.

DNA encoding $V_H$ and $V_L$ of hamster αmurine CD154 were cloned and fused to the human γ 1 $C_H1$, $C_H2$, $C_H3$ region or to described variants. The nucleotide sequences was verified using Megabace™ sequence analyzer. A plasmid expression vector, pEE12 containing both heavy and light chains of each of the MR1 variants will be transfected into NS0 cells and products purified by Protein A chromatography.

Binding to CD154.

Comparison of the binding activity of CD154 antibody variants was determined by their binding to CHO cells transfected with mouse CD154. CD154-expressing CHO cells will be incubated with biotin-labeled αCD154 in the presence of unlabeled αCD154 heavy chain variants or isotype-matched antibodies for 1 hr at 4° C. Binding of biotinylated MR1 will be detected using a streptavidin conjugated fluorochrome and flow cytometry will be performed. The percent of inhibition by variants will be deduced by recording reductions in the mean fluorescence intensity of MR1 stained cells.

Antibody Half-Life Using ELISA

An αhuman IgG1 ELISA will be used to determine the half-life of all the IgG1 variants. Serum concentrations of hIgG1 will be determined over 1 month post-administration.

Binding of Variants to FcRs.

Binding of each of the variant MR1 IgG1 mAbs to FcRs is determined by a solid phase assay. Briefly, Maxisorb ELISA plates will be coated with mouse or human FcγRI, FcγRIIA, FcγRIIB, or FcγRIIIA (R & D Systems). We will prepare biotinylated versions of the MR1 variants γ1 (WT), $γ1^{-C}$ (K322A, P331G, P331G/K322A) and (K322A), $γ1^{-FcR}$ (N325L, K326V, E269R). Other variants will have mutations in both the complement and FcR binding sites. Binding is determined by colorimetric detection using enzyme-coupled avidin. Reduction in binding is determined for each of the variants compared to the WT γ1 molecule.

Binding of αCD154 mAbs to human C1q

Purified human C1q will be titrated into wells in which the IgG1 variants of MR1 have been absorbed onto Maxisorb ELISA plates. Bound C1q will be detected with HRP-chicken anti-C1q. All variants will be compared to the binding of C1q to the WT IgG1 MR1, as described (Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., The contribution of Fc effector mechanisms in the efficacy of anti-CD154 immunotherapy depends on the nature of the immune challenge. Int Immunol 2004. 16: 1583-1594.; and Taylor, P. A., Lees, C. J., Wilson, J. M., Ehrhardt, M. J., Campbell, M. T., Noelle, R. J. and Blazar, B. R., Combined effects of calcineurin inhibitors or sirolimus with anti-CD40L mAb on alloengraftment under non-myeloablative conditions. Blood 2002. 100: 3400-3407.

Induction of tolerance with mutant αCD154 mAbs. The hamster anti-murine CD154 that was produced in our laboratory 40 MR1 routinely induces long-lived graft tolerance, as we have shown (Quezada, S. A., Fuller, B., Jarvinen, L. Z., Gonzalez, M., Blazar, B. R., Rudensky, A. Y., Strom, T. B. and Noelle, R. J., Mechanisms of donor-specific transfusion tolerance: preemptive induction of clonal T-cell exhaustion via indirect presentation. Blood 2003. 102: 1920-1926; Quezada, S. A., Bennett, K., Blazar, B. R., Rudensky, A. Y., Sakaguchi, S. and Noelle, R. J., Analysis of the underlying cellular mechanisms of anti-CD154-induced graft tolerance: the interplay of clonal anergy and immune regulation. J Immunol 2005. 175: 771-779; Rossini, A. A., Parker, D. C., Phillips, N. E., Durie, F. H., Noelle, R. J., Mordes, J. P. and Greiner, D. L., Induction of immunological tolerance to islet allografts. Cell Transplant 1996. 5: 49-52). Tolerance is induced by the co-administration of alloantigen (in the form of donor spleen cells) and αCD154. It has been shown that a humanized IgG1 form of MR1 also induces graft tolerance 24, and therefore the WT al variant will serve as a positive control for tolerance induction. The mutant versions of MR1 which have lost the ability to bind complement will be tested for their ability to induce graft tolerance.

Skin grafting is performed as a modification of a technique used by Markees et al. (See reference citation 12). Briefly, age-matched male CB6F1 mice will be used as donors for both spleen cells (DST) and skin grafts. Recipient C57BL/6 mice will injected with or without 5×107 DST cells in 500 μL Hanks balanced salt solution by tail vein injection (intravenously) and 500 μg of WT or mutant αCD154 or control immunoglobulin, hamster or human, (HIgG1) in phosphate-buffered saline (PBS) intraperitoneally on days −3, −5 and −7. Mice will treated with the appropriate antibody (250 αg/injection) 3 times per week, thereafter for the duration of the experiment. On day 0, recipient mice will be anesthetized with 50 μg per gram body weight of each of ketamine and xylazine injected intraperitoneally (15 mg/mL in PBS), and CB6F1 skin grafts will be prepared using established methods. Rejection will be defined as the day on which less than 20% of the skin graft remains. Animals will be evaluated for skin graft rejection for 100 days. In addition, for each of the tolerant groups, skin grafts will be taken at day 100 and evaluated by histochemistry for leukocyte infiltrates and scored based on the number of cells/area measured. Finally, third party transplants (H-2Kskin) will be transplanted on tolerized mice (in selected groups) to assure that the tolerance induced is antigen specific, as has been published previously in this system (Markees, T. G., Phillips, N. E., Noelle, R. J., Shultz, L. D., Mordes, J. P., Greiner, D. L. and Rossini, A. A., Prolonged survival of mouse skin allografts in recipients treated with donor splenocytes and antibody to CD40 ligand. Transplantation 1997. 64: 329-335, Markees, T., Phillips, N., Gordon, E., Noelle, R. J., Mordes, J. P., Greiner, D. L. and Rossini, A. A., Improved skin allograft tolerance induced by treatment with donor splenocytes and an extended course of anti-CD154 monoclonal antibody. Transplant Proc 1998. 30: 2444-2446; Markees, T. G., Appel, M. C., Noelle, R. J., Mordes, J. P., Greiner, D. L. and Rossini, A. A., Tolerance to islet xenografts induced by dual manipulation of antigen presentation and co-stimulation. Transplantation Proceedings 1996. 28: 814-815) of humoral immunity with mutant αCD154 mAbs.

In addition to measuring the impact of the complement binding mutants (K322A, P331G, P331G/K322A) on tolerance, we also will measure the impact of antibody treatment on the development of primary and secondary humoral immune responses, as previously described. Briefly, mice (4/group) will be immunized with chicken ovalbumin in CFA (200 αg/mouse) and treated with the MR1 variants (200 αg/mouse×3 times/week). On days 7, 14 and 21, IgM and IgG anti-OVA will be measured by a standardized anti-OVA ELISA and serum concentrations of anti-OVA will be quantified. It is anticipated that such variants will be effective at inhibiting humoral immunity.

Toxicity Studies with Mutant αCD154 mAbs.

The thrombogenic activity of αCD154 has been demonstrated in a murine model using mice that express human FcγRIIA. This model parallels toxicity findings in NHP using both intact and aglycosylated forms of anti-human CD154. Briefly, mice will be injected with preformed immune complexes (IC) of sCD154 (R & D Systems) and each variant of αCD154 (138 μg mAb and 50 μg Ag, approximating 500 nM IC at a 1:3 (mAb/Ag) stoichiometric ratio). Following injection, if the mixture is thrombolytic, mice will exhibit prolonged disorientation, shallow breathing, and impaired mobility. Those exhibiting this activity are expected to have marked reductions in platelet counts. After 60 minutes, lungs will be harvested, fixed in formalin, sectioned and H&E-stained. Mouse lung sections will be evaluated for evidence of thrombosis (as measured by intravascular thrombi) and the number of thrombi/section will be counted. For each mouse, 10 sections will be counted and the total number of thrombi compared across all groups treated with the various variants of IgG1 MR1. In addition, total platelet counts (harvested by cardiac puncture at the time of euthanasia), will be evaluated by flow cytometry, and are expected to drop by 80% using those antibodies that are thrombogenic. These findings will determine which of the MR1 variants (FcR binding (N325L, K326V, E269R) are thrombogenic and if alteration of the FcR binding alters this activity.

Blocking the Development of a T Cell Mediated Autoimmune Disease, Experimental Autoimmune Encephalomyelitis (EAE).

It has not been reported that C' activation is critical for anti-CD154 induced protection in EAE. Our data show that short-term intervention leads to long term remission, which suggests that it induces tolerance. It has been reported that $MR1^{aglys}$ inhibits EAE49, however, this specific mAb only had a 50% reduction in C1q. As we have extensive experience in anti-CD154 in treatment of EAE (we will evaluate each of the variants in this disease model) to address the potential of each in blocking cell-mediated immunity.

Female C57BL/6 mice 5-8 weeks old will be immunized subcutaneously with 200 µg of MOG35-55 peptide emulsified in CFA supplemented with 5 mg/ml of *Mycobacterium tuberculosis*. The mice will receive intraperitoneal injections with 250 ng pertussis toxin at the time of immunization and 48 hours later. After 7 days, the mice will receive an identical booster immunization with MOG/CFA without pertussis toxin. Clinical disease usually commences between day 16 and day 20 after immunization. Mice will be administered each of the MR1 variants, human IgG (as control for the variants), hamster Ig (as control for MR1) or hamster MR1 (200 µg/mouse 3×/week) for the duration of the experiment (50 days).

Clinical Evaluation.

Mice will be scored four times per week as follows: 0, no detectable signs of EAE; 0.5, limp distal tail; 1, complete limp tail; 1.5, limp tail and hind limb weakness; 2, unilateral partial hind limb paralysis; 2.5, bilateral partial hind limb paralysis; 3, complete bilateral hind limb paralysis; 3.5, complete hind limb paralysis and unilateral forelimb paralysis; 4, total paralysis of both forelimbs and hind limbs; 5, death. Mice scoring greater than 4 but less than 5 will be euthanized.

Determination of Toxicity

A desired antibody according to the invention will have greatly reduced or no toxicity in the disclosed thrombotic animal model.

Determination of Efficacy

Efficacy (induction of tolerance) will be assessed in the disclosed skin graft model of tolerance.

The following examples illustrate the operability of the invention in developing safe and improved, functionally active anti-CD154 antibodies for use in immune therapies.

Example 1: Design of Anti-CD154 Antibodies with Impaired FcγR Binding Activities And Functional Properties Assessment of the Capacity of MR1 and MR1-Derived Monoclonal Anti-Mouse CD154 Antibodies to Activate Platelets in Mice Transgenic for Human FcγRIIA As discussed herein, in early clinical trials, it was reported that mAbs targeting CD154, which is important in autoimmune and other diseases, displayed an unexpected association with thrombosis (induced blood clots which may cause death or stroke). The mechanisms by which such mAbs are apparently associated with thrombosis were unknown, in part because the disease conditions in which they were used are independently associated with thrombosis. Additionally, there is no known molecular mechanism by which antibodies directly activate coagulation (i.e., the blood clotting system that drives thrombosis); hence, one or more components intermediary between therapeutic mAbs and coagulation per se must be involved. In the case of heparin-induced thrombocytopenia (HIT), a single intermediary component has been identified: the platelet IgG receptor, FcγRIIa.

HIT is a drug-induced thrombotic autoimmune syndrome in which IgG antibodies can induce a thrombotic state in patients—not by directly activating coagulation, but rather by forming immune complexes (ICs) with a platelet antigen target, PF4 (bound to the drug, heparin), and subsequently activating platelet FcγRIIa, which leads to multiple platelet-dependent prothrombotic processes, including coagulation activation and thrombosis. Attempts to replicate HIT's thrombotic processes in a mouse model were hindered by the fact that mice lack the equivalent of the human FcγRIIA gene. McKenzie and colleagues thus made mice transgenic for human FcγRIIa (FCGR2A mice) and went on to demonstrate that the HIT thrombotic phenotype could be fully replicated in FCGR2A mice, but not in mice lacking this IgG receptor McKenzie S E, Taylor S M, Malladi P, Yuhan H, Cassel D L, Chien P, Schwartz E, Schreiber A D, Surrey S, Reilly M P. The role of the human Fc receptor Fc gamma RIIA in the immune clearance of platelets: a transgenic mouse model. J Immunol. 1999; 162:4311-8).

It was later shown that anti-CD154 mAbs, when combined with CD154 (human or mouse), rapidly induced thrombocytopenia and thrombosis in FCGR2A, but not wild type (WT) mice. (Robles-Carrillo L, Meyer T, Hatfield M, Desai H, Dávila M, Langer F, Amaya M, Garber E, Francis J L, Hsu Y M, Amirkhosravi A. Anti-CD154 immune complexes potently activate platelets in vitro and cause thrombosis in FCGR2A transgenic mice. J Immunol. 2010; 185:1577-83). These studies suggested that any therapeutic mAb associated with thrombosis may depend, at least in part, on the activation of the platelet IgG receptor. It will thus be informative to evaluate the platelet-activating capacity of anti-CD154 mAbs being developed for therapeutic uses by treating FCGR2A mice with such mAbs, and subsequently identifying how this affects, if at all, the onset of thrombocytopenia or thrombosis. Such testing will be particularly useful for anti-CD154 mAbs that have been engineered to have reduced capacity for triggering FcγRIIa-dependent platelet activation.

It has been reported that a humanized form of MR1, when combined with its antigen target, mouse CD154, rapidly induced severe thrombocytopenia (loss of circulating platelets) and pulmonary thrombosis in FCGR2A mice. (Robles-Carrillo L, Meyer T, Hatfield M, Desai H, Davila M, Langer F, Amaya M, Garber E, Francis J L, Hsu Y M, Amirkhosravi A. Anti-CD154 immune complexes potently activate platelets in vitro and cause thrombosis in FCGR2A transgenic mice. *J Immunol.* 2010; 185:1577-83) In this same study, an aglycosylated humanized anti-mouse CD154 mAb, MR1, which is presumed to have greatly reduced capacity to activate FcγRIIa, did not induce thrombocytopenia or thrombosis.

In the experiments herein, we tested variants of monoclonal anti-mouse CD154, MR1, and derivatives thereof, in the above-described FCGR2A mouse model of thrombosis. The specific aim of this study was to inject FCGR2A mice with preformed ICs consisting of mouse CD154 plus MR1 or various MR1 derivatives and to identify: (1) any possible evidence of thrombocytopenia, (2) any possible evidence of pulmonary thrombosis, and (3) any possible behavioral signs of thrombotic stress subsequent to IC-induced platelet activation.

Materials and Methods

Materials:

Four anti-mouse CD154 antibodies were tested in FCGR2A mice:

PBS (baseline controls used for comparison with test mAbs, below)

MR1-WT (a humanized MR1 anti-mouse CD154 mAb)

N325L (a variant of MR1-WT)

K326V (a variant of MR1-WT)

E269R (a variant of MR1-WT)

Murine soluble CD154 (or "sCD154") was purchased from Peprotech, Inc. (Rocky Hill, N.J.).

Methods:

Preparation and delivery of immune complexes (IC): Mouse sCD154 (60 µg) was combined with anti-CD154 mAb (175 µg) in PBS to prepare 250 µl volume of mCD154+anti-CD154 IC solution, 200 µL of which was injected intravenously into each FCGR2A mouse within 5 minutes of IC preparation.

Experimental Animals:

Twenty four FCGR2A mice (8-12 week old, male or female) mice were divided into five groups (one per test mAb, and one PBS negative control) of six animals per group. The genotype of all FCGR2A animals used in the study were verified by PCR as per Jax Labs protocol.

Intravenous Injection of IC:

Unanesthetized mice were restrained in a standard mouse restrainer. The lateral tail vein was dilated by warming with a heat lamp. IC solutions were then injected slowly (~10 seconds), and mice were transferred immediately to an empty cage for observation.

Observation of Symptoms:

Following IC injection, each mouse was continuously monitored in isolation for ten minutes. During this period, observers assessed and recorded the mice's locomotion, gait, breathing, and monitored the mice for signs of thrombotic stress (such as disorientation and partial or temporary paralysis). Four categories were used to summarize the complex of symptoms observed in test animals: (1) None—no abnormalities in locomotion, gait, breathing, and no sign of disorientation or paralysis; (2) Mild—no sign of disorientation or paralysis, normal locomotion, but signs of lethargy and rapid breathing; (3) Moderate—lethargy, rapid breathing, disruption of locomotion except following contact by observer; (4) Severe—disorientation, signs of paralysis or complete immobility.

Blood Collection and Platelet Counting:

Ten minutes after IC injection, mice were anesthetized by isoflurane and approximately 500 µl of blood was collected into citrate anticoagulant by cardiac puncture using a 25 gauge needle. Platelet counts were determined electronically using an Coulter Act diff Counter within 2 minutes of blood collection. Platelet counts were adjusted for the volume of citrate in the collection tube and recorded for each animal.

Assessment of Thrombosis in the Pulmonary Vasculature:

Immediately after blood draw, entire lungs were dissected, rinsed in PBS buffer, and placed in buffered formalin. Twenty four hours later, paraffin blocks were prepared and 3 m slide sections were cut and stained with hematoxylin and eosin (H&E) for histological evaluation for the presence of thrombi. Five slides were prepared from the mid-organ region of each lung with spacing between cut section of approximately 50-100 µm. Each slide was assessed by two independent observers blinded to the identity of the animal groups from which the slides were prepared. Five randomly chosen fields were assessed per slide. In cases where greater than 9 thrombi were observed per field, no attempt was made to determine the precise number of thrombi, and the value of 10 (ten) was entered as the nominal observation.

Statistical Analysis:

Data were analyzed by SigmaPlot. Platelet counts and number of clots/field between groups were analyzed using the Kruskal-Wallis One Way Analysis of Variance on Ranks Results The first group of animals were injected with PBS (200 µL delivered) in order to obtain baseline platelet counts and normal lungs for histological analysis. These values are compared below to test animal groups. Following PBS injection, all animals exhibited normal locomotion, gait, breathing, and showed no signs of thrombotic stress (such as disorientation and partial or temporary paralysis). Animals injected with MR1-WT mAb showed signs of moderate to severe signs of thrombotic stress (FIG. 6), which correlated with loss of circulating platelets (FIG. 7), and histologic observation of the prevalence of pulmonary thrombi (FIG. 8). The injection of animals with N325L and K326V mAbs gave similar results (did not prevent thrombosis). In many cases, histologic evidence of thrombosis greatly exceeded 10 clots per field. All animals injected with E269R mAb exhibited normal locomotion, gait, breathing, and showed no signs of thrombotic stress. The lung vasculature of all E269R-injected mice were free of thrombi. (See histologic data also in FIGS. 9-13)

It should be noted that two of six mice injected with N325L did not experience thrombotic thrombocytopenia. The causes of these anomalies are unknown; however, in our experience, such occasional outliers can occur in experiments of this type. On the other hand, because the platelet counts correlated with the relative absence of pulmonary thrombi from these two mice, the data were included in the statistical analysis comparing the experimental groups.

Conclusions

In this mouse model of antibody-induced thrombocytopenia and thrombosis, MR1-WT, N325L, and K326V demonstrated potent activity, whereas E269R lacked activity and was comparable by all measures with the PBS negative control group.

Example 2: Design of Anti-CD154 Antibodies with Impaired Complement Dependent Cytotoxicity (CDC) Activities and Functional Properties Cloning and Synthesis of Chimeric Anti-CD154 Antibody (MR1) with Human IgG Constant Regions It was initially theorized by the present inventor, in part based on prior literature, that anti-CD154 antibodies lose their ability to induce tolerance when the C1q binding site is mutated Based thereon, we assumed that a model anti-CD154 antibody, i.e., the murine anti-CD154 (MR1) having the variable heavy and light sequences in FIG. 2 would lose its ability to induce tolerance when the C1q binding site is mutated.

To this end, MR1 was converted into a human IgG1. It has previously reported that a human IgG1 version of MR1 can induce tolerance (Daley, S. R., Cobbold, S. P. & Waldmann, H. Fc-disabled anti-mouse CD154 antibodies retain efficacy in promoting transplantation tolerance. *Am J Transplant* 8, 2265-2271 (2008)). As described below a chimeric hIgG1 form of MR1 was produced and then engineered to introduce mutations in the hIgG1 Fc region that disrupt C1q binding.

The first step in engineering the hamster anti-murine CD154 into a human IgG1 (MR1 hIgG1) is to clone and sequence the light and heavy chains of MR1. DNA encoding VH and VL of hamster anti-CD154 MR1 have been cloned and fused to the human γ 1 CH1, CH2, CH3 region or to variants described below. The nucleotide sequences have been verified using Megabace™ sequence analyzer and are shown in FIG. 2. A plasmid expression vector, pEE12 containing both light and heavy chains of each of the MR1 variants was transfected into NS0 cells and products purified by Protein A chromatography.

The generation and characterization of a series of C' variants of the hIgG1 form of MR1 was then effected.

Designing Fc Variants with Impaired CDC.

No single or combinations of Fc mutations have been reported to ablate the CDC activity while maintaining near wild type ADCC activity. However, CDC assay conditions may effect this analysis. For example, CDC activities can differ significantly depending on target cells, dilution factors of the complement, and species sources of the complement which could be from human, guinea pig, or rabbit as well as other factors. Given our analysis we believe that the best single and double mutation candidates for impaired CDC activity without significant effects on ADCC are: K322A, P331G, and P331/K322A.

Mutagenesis of K322A and P331G of IgG1 have been shown to abrogate complement activation. It has been shown that this variant binds human complement C1q with greatly lowered affinity and inefficiently activates human C'. (Hessell, A. J., et al. Fc receptor but not complement binding is important in antibody protection against HIV. *Nature* 449, 101-104 (2007)).

Measurement of Loss of C1q Binding by MR1 hIgG1 Mutants.

The binding of C1q to each of the MR1 hIgG1 mutants was evaluated. For measuring C1q binding to MR1, purified MR1 variant antibody (Aragen Bioscience, Morgan Hill, Calif.), was diluted to 100, 10, 1 and 0.1 μg/ml in phosphate-buffered saline (PBS) to coat a 96-well enzyme-linked immunosorbent assay (ELISA)-grade plate (ThermoScientific, Florence, Ky.) overnight at 4° C. The plate was then washed three times with PBS-0.05% Tween 20 (Tw20) and blocked for 1 h with 1% bovine serum albumin (BSA)-Tw20-PBS at room temperature. Complement component C1q from human serum (Sigma, St. Louis, Mo.), was diluted to 1 μg/ml in 1% BSA-Tw20-PBS then plated and allowed to incubate for 1 h at room temperature. The plate was washed three times with PBS-Tw20, and horseradish peroxidase-labeled sheep anti-human C1q (GenWay Biotech, San Diego, Calif.) was added. After a 1 h, room temperature incubation, the plate was washed three times with PBS-Tw20, then TMB (3,3',5,5'-tetramethylbenzidine) (Thermo-Scientific) provided a colorimetric change which was then quantitated at 450 nm by an ELISA reader (BioTek, Winooski, Vt.).

Figure 4:
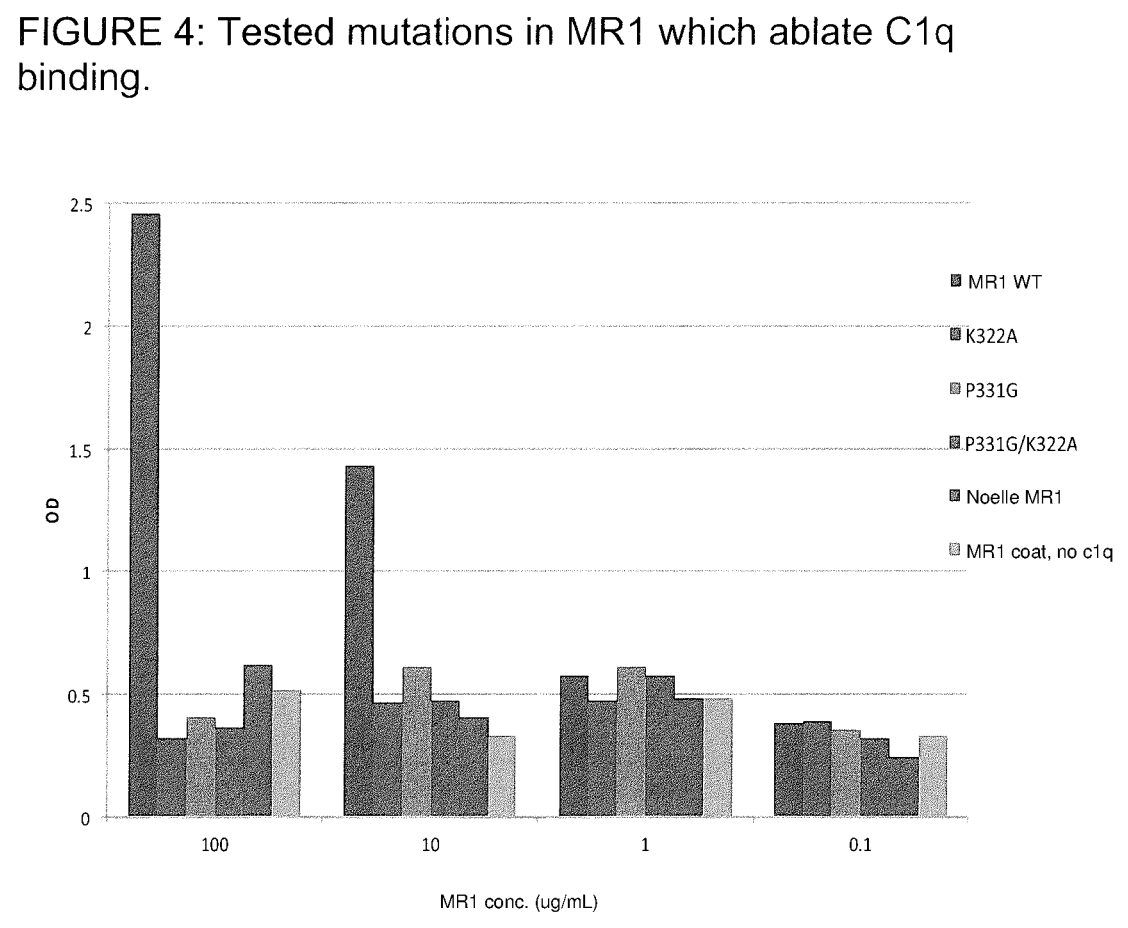

The results of these experiments are in FIG. 4. As shown therein, all of the mutants had reduced C1q binding.

Functional Studies with Mutant Anti-CD154 Mabs.

The hamster anti-murine CD154 that was produced in our laboratory 3MR1 routinely induces long-lived graft tolerance, as we have shown (Noelle, R. J., et al. A novel ligand on activated T helper cells binds CD40 and transduces the signal for the cognate activation of B cells. Proc. Natl. Acad. Sci. USA89, 6550-6554 (1992)).

However, previous reports have suggested that in complement deficient animals that anti-CD154 antibodies do not elicit tolerance. (Quezada, S. A., et al. Analysis of the underlying cellular mechanisms of anti-CD154-induced graft tolerance: the interplay of clonal anergy and immune regulation. *J Immunol* 175, 771-779 (2005); Quezada, S. A., et al. Mechanisms of donor-specific transfusion tolerance: preemptive induction of clonal T-cell exhaustion via indirect presentation. *Blood* 102, 1920-1926 (2003).; Quezada, S. A., Jarvinen, L. Z., Lind, E. F. & Noelle, R. J. CD40/CD154 Interactions at the Interface of Tolerance and Immunity. *Annu Rev Immunol* 22, 307-328 (2004); Rossini, A. A., et al. Induction of immunological tolerance to islet allografts. *Cell Transplant* 5, 49-52 (1996).) Therefore, we assessed whether our mutants were able to elicit tolerance. In these experiments, the four hIgG1 versions of MR1 (MR1 WT, K322A, P331G, and P331/K322A) were tested for their ability to induce graft tolerance and the results of these experiments are in FIG. 5.

Said skin grafting was effected using a modification of the technique developed by Markees et al. (Markees, T. G., et al. Prolonged survival of mouse skin allografts in recipients treated with donor splenocytes and antibody to CD40 ligand. *Transplantation* 64, 329-335 (1997)). Briefly, age-matched male $CB6F_1$ mice were used as donors of both spleen cells (DST) and skin grafts. More specifically, Tail skin (μl cm2) from CB6F1 (F1) female donors was transplanted onto the dorsal area of age-matched C57BL/6 females. To induce T cell tolerance, recipients received T-depleted spleen cells (DST) by IV tail injection from F1 donors on day −7 before skin graft (day 0) and 200 μg of MR-1 variants IP on days −7, −5, and −3. Grafts were observed 3 times per week starting on day 8. Grafts were considered rejected when 80% of the original graft disappeared or became necrotic.

Recipient mice were injected with or without $5\times10^7$ DST cells in 500 μL Hanks balanced salt solution by tail vein injection (intravenously) and 500 μg of anti-CD154 or control hamster immunoglobulin (H-Ig) in phosphate-buffered saline (PBS) intraperitoneally. Mice were injected with the MR1 variants or H-Ig 3 times per week for the duration of the experiment. On day 0, recipient mice were anesthetized with 50 μg per gram body weight of each of ketamine and xylazine injected intraperitoneally (15 mg/mL in PBS), and $CB6F_1$ or C57BL/6 skin grafts were prepared using established methods. Rejection was defined as the day on which less than 20% of the skin graft remained.

Afterward the results were analyzed. Treatment with control human IgG1 and DST did not prolong rejection, as was anticipated. However, as can be seen in FIG. 6, like WT H IgG1 MR1, all of the mutant MR1 antibodies induced long lived graft acceptance. Hence, C1q binding and complement activation by anti-CD154 antibodies IS NOT essential to induce graft tolerance. This is in contrast to what was observed in the complement deficient mice, and suggests that the complement deficient mice likely have some other anomalies that influence the induction of graft tolerance. Thus, therapeutically effective αCD154 antibodies can be produced that do not bind complement.

REFERENCES CITED IN APPLICATION

The following references are cited. The contents of all are incorporated by reference herein.

1 Noelle, R. J., Mackey, M., Foy, T., Buhlmann, J. and Burns, C., CD40 and its ligand in autoimmunity. Ann N Y Acad Sci 1997. 815: 384-391.

2 Mackey, M. F., Barth, R. J., Jr. and Noelle, R. J., The role of CD40/CD154 interactions in the priming, differentiation, and effector function of helper and cytotoxic T cells. J Leukoc Biol 1998. 63: 418-428.

3 Noelle, R. J., CD40 and its ligand in cell-mediated immunity. Agents Actions Suppl 1998. 49: 17-22.

4 Quezada, S. A., Jarvinen, L. Z., Lind, E. F. and Noelle, R. J., CD40/CD154 Interactions at the Interface of Tolerance and Immunity. Annu Rev Immunol 2004. 22: 307-328.

5 Kenyon, N. S., Chatzipetrou, M., Masetti, M., Ranuncoli, A., Oliveira, M., Wagner, J. L., Kirk, A. D., Harlan, D. M., Burkly, L. C. and Ricordi, C., Long-term survival and function of intrahepatic islet allografts in rhesus monkeys treated with humanized anti-CD154. Proc Natl Acad Sci USA 1999. 96: 8132-8137.

6 Kirk, A. D., Burkly, L. C., Batty, D. S., Baumgartner, R. E., Berning, J. D., Buchanan, K., Fechner, J. H., Jr., Germond, R. L., Kampen, R. L., Patterson, N. B., Swanson, S. J., Tadaki, D. K., TenHoor, C. N., White, L., Knechtle, S. J. and Harlan, D. M., Treatment with humanized monoclonal antibody against CD154 prevents acute renal allograft rejection in nonhuman primates. Nat Med 1999. 5: 686-693.

7 Sidiropoulos, P. I. and Boumpas, D. T., Lessons learned from anti-CD40L treatment in systemic lupus erythematosus patients. Lupus 2004. 13: 391-397.

8 Sidiropoulos, P. I. and Boumpas, D. T., Lessons learned from anti-CD40L treatment in systemic lupus erythematosus patients. Lupus 2004. 13: 391-397.

9 Ferrant, J. L., Benjamin, C. D., Cutler, A. H., Kalled, S. L., Hsu, Y. M., Garber, E. A., Hess, D. M., Shapiro, R. I., Kenyon, N. S., Harlan, D. M., Kirk, A. D., Burkly, L. C. and Taylor, F. R., The contribution of Fc effector mechanisms in the efficacy of anti-CD154 immunotherapy depends on the nature of the immune challenge. Int Immunol 2004. 16: 1583-1594.

10 U.S. Pat. No. 6,444,018

11 Gordon, E. J., Markees, T. G., Phillips, N. E., Noelle, R. J., Shultz, L. D., Mordes, J. P., Rossini, A. A. and Greiner, D. L., Prolonged survival of rat islet and skin xenografts in mice treated with donor splenocytes and anti-CD154 monoclonal antibody. Diabetes 1998. 47: 1199-1206.

12 Markees, T. G., Phillips, N. E., Noelle, R. J., Shultz, L. D., Mordes, J. P., Greiner, D. L. and Rossini, A. A., Prolonged survival of mouse skin allografts in recipients treated with donor splenocytes and antibody to CD40 ligand. Transplantation 1997. 64: 329-335.

13 Jarvinen, L. Z., Blazar, B. R., Adeyi, 0. A., Strom, T. B. and Noelle, R. J., CD154 on the surface of CD4+CD25+ regulatory T cells contributes to skin transplant tolerance. Transplantation 2003. 76: 1375-1379.

14 Quezada, S. A., Fuller, B., Jarvinen, L. Z., Gonzalez, M., Blazar, B. R., Rudensky, A. Y., Strom, T. B. and Noelle, R. J., Mechanisms of donor-specific transfusion tolerance: preemptive induction of clonal T-cell exhaustion via indirect presentation. Blood 2003. 102: 1920-1926.

15 Frleta, D., Lin, J. T., Quezada, S. A., Wade, T. K., Barth, R. J., Noelle, R. J. and Wade, W. F., Distinctive maturation of in vitro versus in vivo anti-CD40 mAb-matured dendritic cells in mice. J Immunother 2003. 26: 72-84.

16 Quezada, S., Eckert, M., Schned, A., Noelle, R. J. and Burns, C., Distinct mechanisms of action of anti-CD154 in early versus late treatment of murine lupus nephritis. Arth Rheum. 2003. in press.

17 Elster, E. A., Xu, H., Tadaki, D. K., Montgomery, S., Burkly, L. C., Berning, J. D., Baumgartner, R. E., Cruzata, F., Marx, R., Harlan, D. M. and Kirk, A. D., Treatment with the humanized CD154-specific monoclonal antibody, hu5C8, prevents acute rejection of primary skin allografts in nonhuman primates. Transplantation 2001. 72: 1473-1478.

18 Benda, B., Ljunggren, H. G., Peach, R., Sandberg, J. O. and Korsgren, O., Co-stimulatory molecules in islet xenotransplantation: CTLA4Ig treatment in CD40 ligand-deficient mice. Cell transplantation 2002. 11: 715-720.

19 Wekerle, T. and Sykes, M., Mixed chimerism and transplantation tolerance. Annual review of medicine 2001. 52: 353-370.

20 Camirand, G., Caron, N. J., Turgeon, N. A., Rossini, A. A. and Tremblay, J. P., Treatment with anti-CD154 antibody and donor-specific transfusion prevents acute rejection of myoblast transplantation. Transplantation 2002. 73: 453-461.

21 Tung, T. H., Mackinnon, S. E. and Mohanakumar, T., Long-term limb allograft survival using anti-CD40L antibody in a murine model. Transplantation 2003. 75: 644-650.

22 Koyama, I., Kawai, T., Andrews, D., Boskovic, S., Nadazdin, O., Wee, S. L., Sogawa, H., Wu, D. L., Smith, R. N., Colvin, R. B., Sachs, D. H. and Cosimi, A. B., Thrombophilia associated with anti-CD154 monoclonal antibody treatment and its prophylaxis in nonhuman primates. Transplantation 2004. 77: 460-462.

23 Kawai, T., Andrews, D., Colvin, R. B., Sachs, D. H. and Cosimi, A. B., Thromboembolic complications after treatment with monoclonal antibody against CD40 ligand. Nat Med 2000. 6: 114.

24 Daley, S. R., Cobbold, S. P. and Waldmann, H., Fc-disabled anti-mouse CD40L antibodies retain efficacy in promoting transplantation tolerance. Am J Transplant 2008. 8: 2265-2271.

25 Sanchez-Fueyo, A., Domenig, C., Strom, T. B. and Zheng, X. X., The complement dependent cytotoxicity (CDC) immune effector mechanism contributes to anti-CD154 induced immunosuppression. Transplantation 2002. 74: 898-900.

26 Monk, N. J., Hargreaves, R. E., Marsh, J. E., Farrar, C. A., Sacks, S. H., Millrain, M., Simpson, E., Dyson, J. and Jurcevic, S., Fc-dependent depletion of activated T cells occurs through CD40L-specific antibody rather than costimulation blockade. Nat Med 2003. 9: 1275-1280.

27 Truscott, S. M., Abate, G., Price, J. D., Kemper, C., Atkinson, J. P. and Hoft, D. F., CD46 engagement on human CD4+ T cells produces T regulatory type 1-like regulation of antimycobacterial T cell responses. Infection and immunity 2010. 78: 5295-5306.

28 Cardone, J., Le Friec, G., Vantourout, P., Roberts, A., Fuchs, A., Jackson, I., Suddason, T., Lord, G., Atkinson, J. P., Cope, A., Hayday, A. and Kemper, C., Complement regulator CD46 temporally regulates cytokine production by conventional and unconventional T cells. Nature immunology 2010. 11: 862-871.

29 Fuchs, A., Atkinson, J. P., Fremeaux-Bacchi, V. and Kemper, C., CD46-induced human Treg enhance B-cell responses. European journal of immunology 2009. 39: 3097-3109.

30 Alford, S. K., Longmore, G. D., Stenson, W. F. and Kemper, C., CD46-induced immunomodulatory CD4+ T cells express the adhesion molecule and chemokine receptor pattern of intestinal T cells. Journal of immunology 2008. 181: 2544-2555.

31 Barchet, W., Price, J. D., Cella, M., Colonna, M., MacMillan, S. K., Cobb, J. P., Thompson, P. A., Murphy, K. M., Atkinson, J. P. and Kemper, C., Complement-induced regulatory T cells suppress T-cell responses but allow for dendritic-cell maturation. Blood 2006. 107: 1497-1504.

32 Liszewski, M. K., Kemper, C., Price, J. D. and Atkinson, J. P., Emerging roles and new functions of CD46. Springer seminars in immunopathology 2005. 27: 345-358.

33 Kawai, T., Andrews, D., Colvin, R. B., Sachs, D. H. and Cosimi, A. B., Thromboembolic complications after treatment with monoclonal antibody against CD40 ligand [In Process Citation]. Nat Med 2000. 6: 114.

34 Langer, F., Ingersoll, S. B., Amirkhosravi, A., Meyer, T., Siddiqui, F. A., Ahmad, S., Walker, J. M., Amaya, M., Desai, H. and Francis, J. L., The role of CD40 in CD40L- and antibody-mediated platelet activation. Thrombosis and haemostasis 2005. 93: 1137-1146.

35 Robles-Carrillo, L., Meyer, T., Hatfield, M., Desai, H., Davila, M., Langer, F., Amaya, M., Garber, E., Francis, J. L., Hsu, Y. M. and Amirkhosravi, A., Anti-CD40L 36 Couzin, J., Drug discovery. Magnificent obsession. Science 2005. 307: 1712-1715.
37 Hessell, A. J., Hangartner, L., Hunter, M., Havenith, C. E., Beurskens, F. J., Bakker, J. M., Lanigan, C. M., Landucci, G., Forthal, D. N., Parren, P. W., Marx, P. A. and Burton, D. R., Fc receptor but not complement binding is important in antibody protection against HIV. Nature 2007. 449: 101-104.
38 Armour, K. L., Clark, M. R., Hadley, A. G. and Williamson, L. M., Recombinant human IgG molecules lacking Fcgamma receptor I binding and monocyte triggering activities. Eur J Immunol 1999. 29: 2613-2624.
39 Taylor, P. A., Lees, C. J., Wilson, J. M., Ehrhardt, M. J., Campbell, M. T., Noelle, R. J. and Blazar, B. R., Combined effects of calcineurin inhibitors or sirolimus with anti-CD40L mAb on alloengraftment under nonmyeloablative conditions. Blood 2002. 100: 3400-3407.
40 Noelle, R. J., Roy, M., Shepherd, D. M., Stamenkovic, I., Ledbetter, J. A. and Aruffo, A., A novel ligand on activated T helper cells binds CD40 and transduces the signal for the cognate activation of B cells. Proc. Natl. Acad. Sci. USA 1992. 89: 6550-6554.
41 Quezada, S. A., Bennett, K., Blazar, B. R., Rudensky, A. Y., Sakaguchi, S. and Noelle, R. J., Analysis of the underlying cellular mechanisms of anti-CD154-induced graft tolerance: the interplay of clonal anergy and immune regulation. J Immunol 2005. 175: 771-779.
42 Rossini, A. A., Parker, D. C., Phillips, N. E., Durie, F. H., Noelle, R. J., Mordes, J. P. and Greiner, D. L., Induction of immunological tolerance to islet allografts. Cell Transplant 1996. 5: 49-52.
43 Markees, T., Phillips, N., Gordon, E., Noelle, R. J., Mordes, J. P., Greiner, D. L. and Rossini, A. A., Improved skin allograft tolerance induced by treatment with donor splenocytes and an extended course of anti-CD154 monoclonal antibody. Transplant Proc 1998. 30: 2444-2446.
44 Markees, T. G., Appel, M. C., Noelle, R. J., Mordes, J. P., Greiner, D. L. and Rossini, A. A., Tolerance to islet xenografts induced by dual manipulation of antigen presentation and co-stimulation. Transplantation Proceedings 1996. 28: 814-815.
45 van den Eertwegh, A. J., Van Meurs, M., Foy, T. M., Noelle, R. J., Boersma, W. J. and Claassen, E., In vivo gp39-CD40 interactions occur in the non-follicular compartments of the spleen and are essential for thymus dependent antibody responses and germinal center formation. Adv Exp Med Biol 1994. 355: 75-80.
46 van, den, Eertwegh, Aj, Van, M. M., Foy, T. M., Noelle, R. J., Boersma, W. J. and Claassen, E., In vivo gp39-CD40 interactions occur in the non-follicular compartments of the spleen and are essential for thymus dependent antibody responses and germinal center formation. Advances in experimental medicine and biology 1994. 355: 75-80.
47 Foy, T. M., Laman, J. D., Ledbetter, J. A., Aruffo, A., Claassen, E. and Noelle, R. J., gp39-CD40 interactions are essential for germinal center formation and the development of B cell memory. J. Exp. Med. 1994. 180: 157-164.
48 Gerritse, K., Laman, J. D., Noelle, R. J., Aruffo, A., Ledbetter, J. A., Boersma, W. J. and Claassen, E., CD40-CD40 ligand interactions in experimental allergic encephalomyelitis and multiple sclerosis. National Academy of Sciences, Washington, D.C., Proceedings of the National Academy of Sciences 1996. 93: 2499-2504.
49 Nagelkerken, L., Haspels, I., van Rijs, W., Blauw, B., Ferrant, J. L., Hess, D. M., Garber, E. A., Taylor, F. R. and Burkly, L. C., FcR interactions do not play a major role in inhibition of experimental autoimmune encephalomyelitis by anti-CD154 monoclonal antibodies. J Immunol 2004. 173: 993-999.
50 Becher, B., Durell, B. G. and Noelle, R. J., Experimental autoimmune encephalitis and inflammation in the absence of interleukin-12. J Clin Invest 2002. 110: 493-497.
51 Becher, B., Durell, B. G., Miga, A. V., Hickey, W. F. and Noelle, R. J., The clinical course of experimental autoimmune encephalomyelitis and inflammation is controlled by the expression of CD40 within the central nervous system. J Exp Med 2001. 193: 967-974.
52 Howard, L. M., Miga, A. J., Vanderlugt, C. L., Dal Canto, M. C., Laman, J. D., Noelle, R. J. and Miller, S. D., Mechanisms of immunotherapeutic intervention by anti-CD40L (CD154) antibody in an animal model of multiple sclerosis. J Clin Invest 1999. 103: 281-290.

The invention claimed is:

1. A method of inducing immunosuppression without eliciting thrombotic events in a patient in need thereof comprising administering to a patient an effective amount of a human or humanized antibody of the human IgG1 isotype that specifically binds human CD154 wherein said antibody contains light chain CDR1, CDR2 and CDR3 polypeptides respectively comprising the polypeptide sequences of SEQ ID NO's: 17, 18 and 19, and heavy chain CDR1, CDR2 and CDR3 polypeptides respectively comprising the polypeptide sequences of SEQ ID NO's: 24, 25 and 26, wherein the Fc region of the IgG1 antibody contains an E269R mutation which impairs FcR binding and a mutation which impairs $C_{1q}$ binding activity which is selected from the group consisting of K322A, P331G, and P331G/K322A and further comprises another mutation which impairs binding to an Fc receptor which mutation is K326V.

2. A method of treating autoimmunity, allergy, transplant, GVHD, or inflammation in a patient in need thereof by administering an effective amount of a human or humanized antibody of the human IgG1 isotype that specifically binds human CD154 wherein said antibody contains light chain CDR1, CDR2 and CDR3 polypeptides respectively comprising the polypeptide sequences of SEQ ID NO's: 17, 18 and 19, and heavy chain CDR1, CDR2 and CDR3 polypeptides respectively comprising the polypeptide sequences of SEQ ID NO's: 24, 25 and 26, wherein the Fc region of the IgG1 antibody contains an E269R mutation which impairs FcR binding and a mutation which impairs $C_{1q}$ binding activity which is selected from the group consisting of K322A, P331G, and P331G/K322A and further comprises another mutation which impairs binding to an Fc receptor which mutation is K326V.

3. The method of claim 1 which further includes administration of an antigen.

4. The method of claim 2 which further includes administration of an antigen.

5. The method of claim 1, wherein the patient comprises an autoimmune disease or allergy condition selected from rheumatoid arthritis, Myasthenia gravis, systemic lupus erythematosus, Graves' disease, idiopathic thrombocytopenia purpura, hemolytic anemia, diabetes mellitus, psoriasis, Addison's disease, multiple sclerosis, lupus, inflammatory bowel disorder, asthma and drug-induced asthma.

6. The method of claim 2, wherein the patient has a condition selected from rheumatoid arthritis, Myasthenia gravis, systemic lupus erythematosus, Graves' disease, idiopathic thrombocytopenia purpura, hemolytic anemia, diabetes mellitus, psoriasis, Addison's disease, multiple sclerosis, lupus, inflammatory bowel disorder, asthma and drug-induced asthma.

7. The method of claim 1, wherein the mutation which impairs $C_{1q}$ binding activity is a K322A mutation.

8. The method of claim 1, wherein the mutation which impairs $C_{1q}$ binding activity is a P331G mutation.

9. The method of claim 1, wherein the mutation which impairs $C_{1q}$ binding activity is a P331G/K322A mutation.

10. The method of claim 2, wherein the mutation which impairs $C_{1q}$ binding activity is a K322A mutation.

11. The method of claim 2, wherein the mutation which impairs $C_{1q}$ binding activity is a P331G mutation.

12. The method of claim 2, wherein the mutation which impairs C1q binding activity is a P331G/K322A mutation.

* * * * *

SEQUENCE LISTING

<160> NUMBER OF SEQ ID NOS: 26

<210> SEQ ID NO 1
<211> LENGTH: 949
<212> TYPE: DNA
<213> ORGANISM: Artificial Sequence
<220> FEATURE:
<223> OTHER INFORMATION: CD154 kappa cDNA

<400> SEQUENCE: 1

```
gaagcatcat cagacaggca ctggagcaaa atggagtcac acaatgaggt ccttgtgacc      60
ctgctgctct gggtgtctgg tgcctgtgca gatatcgtgc tgacacagtc tccatcttcc     120
ttggctgtgt ccgcaggaga caaggtcacc atcaactgca agtccagtca gagtctttta     180
tctggtggct ataactactt ggcttggtac cagcagaaaa cagggcagtc tcctaaatta     240
ctgatctatt tcacatccac tcggcacact ggtgtccctg atcgcttcat aggcagtggg     300
tctgggacag atttcactct aaccatcaac agtttccaga ctgaggatct gggagattac     360
```

```
tattgtcagc atcattacgg tactcctctc acgttcggtg atggcaccaa gctggagata      420
aaacgggctg atgctaagcc aaccgtctcc atcttcccac catccagtga gcagttgggc      480
actggaagtg ccacacttgt gtgcttcgtg aacaacttct accccaaaga catcaatgtc      540
aagtggaaag tagatggcag tgaaaaacga gatggcgtcc tgcagagtgt cactgatcag      600
gacagcaaag acagcaccta cagcctgagc agcaccctct cgctgaccaa gcagattat       660 gagaggcata acctgtatac ctgtgaggtt actcataaga catcaactgc agccattgtc      720
aagaccctga acaggaatga gtgttagagc cagaggtcct gaggcaccac cacctgctcc      780
ctaggaccat tctcagtctt ccctcctaag gtcttggagc tttcttcata gacaacctac      840
cactgttgca gtcctccaaa cccccaccac ctcatctccc tcccttttcct tggcttttat     900 catgctaata tttggggaag atattgaata aagtgaatca ttgcacttg                  949

<210> SEQ ID NO 2
<211> LENGTH: 721
<212> TYPE: DNA
<213> ORGANISM: Artificial Sequence
<220> FEATURE:
<223> OTHER INFORMATION: CD154 heavy chain

<400> SEQUENCE: 2
gaacatgtta tcagtgtgct ctccacagtc actgagcaca caggtcttca ccatggtatg       60
gggcttgatc atcatcttcc tggtcacagc aggtacaggt gtccactccc aggtccagtt      120
gaagcagtct ggggctgagt tgtgaagcc tggagcctca gtgaagatat cctgcaaaac       180
ttcaggctat accttcactg atggctacat gaactgggtt gagcagaagc ctgggcaggg      240
ccttgagtgg attggaagaa ttgatcctga tagtggtgat actaggtaca atcagaagtt      300
ccagggcaag gccacactga ctagagacaa atcctccagc acagtctaca tggacctcag      360
gagtctgaca tctgaggact ctgctgtcta ttactgtgcg agagcccctt atatagcgga      420
tataggggag gcctttgatt actggggcca aggaaccatg gtcaccgtct cctcagctgg      480
aagaacagcc ccatctgtct atcccttggc ccctgcctgt gacagcacaa ccagcaccac      540
ggacacggtg accctgggat gcctggtcaa gggctatttc cctgagccgg tgaccgtaag      600
ctggaactct ggagccctga ccagcggtgt gcacaccttc ccatctgtcc tgcgttctgg      660
gctctactcc ctcagcagct cagtgactgt atcttccagc acctggccca gccagactat      720
c                                                                      721

<210> SEQ ID NO 3
<211> LENGTH: 411
<212> TYPE: DNA
<213> ORGANISM: Artificial Sequence
<220> FEATURE:
<223> OTHER INFORMATION: IDEC-131 Humanized Variable Light Region 1

<400> SEQUENCE: 3
agatctctca ccatgggctt caagatggag tcacagtttc tggcctttgt attcgcgttt       60
ctctggttgt ctggtgttga tggagacatt gtgatgaccc agtctccatc tttcctctcc      120
gcctccgtag agacagggt caccatcacc tgcaaggcca gtcagaatgt gattactgct       180
gtagcctggt atcaacagaa accaggaaag tctcctaaat tgctgattta ctcggcatcc      240
aatcggtaca ctggagtccc tgatcgcttc tcaggcagtg gtctgggac agatttcact       300 ctcaccatca gctctctcca gccagaagac ttcgcagatt atttctgcca gcaatataac      360
```

```
agctatccgt acacgttcgg agggggacc aagctggaaa tcaaacgtac g        411
```

```
<210> SEQ ID NO 4
<211> LENGTH: 133
<212> TYPE: PRT
<213> ORGANISM: Artificial Sequence
<220> FEATURE:
<223> OTHER INFORMATION: IDEC-131 Humanized Variable Light Region 1

<400> SEQUENCE: 4
```

Met Gly Phe Lys Met Glu Ser Gln Phe Leu Ala Phe Val Phe Ala Phe
1               5                   10                  15

Leu Trp Leu Ser Gly Val Asp Gly Asp Ile Val Met Thr Gln Ser Pro
            20                  25                  30

Ser Phe Leu Ser Ala Ser Val Gly Asp Arg Val Thr Ile Thr Cys Lys
        35                  40                  45

Ala Ser Gln Asn Val Ile Thr Ala Val Ala Trp Tyr Gln Gln Lys Pro
    50                  55                  60

Gly Lys Ser Pro Lys Leu Leu Ile Tyr Ser Ala Ser Asn Arg Tyr Thr
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Pro Glu Asp Phe Ala Asp Tyr Phe Cys
            100                 105                 110

Gln Gln Tyr Asn Ser Tyr Pro Tyr Thr Phe Gly Gly Gly Thr Lys Leu
        115                 120                 125

Glu Ile Lys Arg Thr
    130

```
<210> SEQ ID NO 5
<211> LENGTH: 411
<212> TYPE: DNA
<213> ORGANISM: Artificial Sequence
<220> FEATURE:
<223> OTHER INFORMATION: IDEC-131 Humanized Variable Light Region 2

<400> SEQUENCE: 5
```

```
agatctctca ccatgggctt caagatggag tcacagtttc tggcctttgt attcgcgttt      60
ctctggttgt ctggtgttga tggagacatt gtgatgaccc agtctccaga ttctctcgcc     120
gtgtccctcg gagagagggc caccatcaac tgcaaggcca gtcagaatgt gattactgct     180
gtagcctggt atcaacagaa accaggacaa tctcctaaat tgctgattta ctcggcatcc     240
aatcggtaca ctggagtccc tgatcgcttc tcaggcagtg gtctgggac agatttcact      300 ctcaccatca gctctctcca ggccgaagac gtggcagatt atttctgcca gcaatataac     360
agctatccgt acacgttcgg agggggacc aagctggaaa tcaaacgtac g               411
```

```
<210> SEQ ID NO 6
<211> LENGTH: 133
<212> TYPE: PRT
<213> ORGANISM: Artificial Sequence
<220> FEATURE:
<223> OTHER INFORMATION: IDEC-131 Humanized Variable Light Region 2

<400> SEQUENCE: 6
```

Met Gly Phe Lys Met Glu Ser Gln Phe Leu Ala Phe Val Phe Ala Phe
1               5                   10                  15

Leu Trp Leu Ser Gly Val Asp Gly Asp Ile Val Met Thr Gln Ser Pro
            20                  25                  30

Asp Ser Leu Ala Val Ser Leu Gly Glu Arg Ala Thr Ile Asn Cys Lys
            35                  40                  45

Ala Ser Gln Asn Val Ile Thr Ala Val Ala Trp Tyr Gln Gln Lys Pro
 50                  55                  60

Gly Gln Ser Pro Lys Leu Leu Ile Tyr Ser Ala Ser Asn Arg Tyr Thr
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Asp Tyr Phe Cys
            100                 105                 110

Gln Gln Tyr Asn Ser Tyr Pro Tyr Thr Phe Gly Gly Gly Thr Lys Leu
            115                 120                 125

Glu Ile Lys Arg Thr
    130

<210> SEQ ID NO 7
<211> LENGTH: 426
<212> TYPE: DNA
<213> ORGANISM: Artificial Sequence
<220> FEATURE:
<223> OTHER INFORMATION: IDEC-131 Humanized Variable Heavy Region 1

<400> SEQUENCE: 7
gtcgacatga tggtgttaag tcttctgtac ctgttgacag cccttccggg tttcctgtca      60
gaggtgcagc ttcaggagtc aggacctggc ctcgtgaaac cttctgagac tctgtccctc     120
acctgtaccg tctctggcga ctccatcact aatggtttct ggatctggat ccggaaacca     180
ccagggaata aacttgagta catgggctac ataagttaca gtggtagcac ttactacaat     240
ccatctctca agagtcgaat ctccatctct cgcgacacat ccaagaacca gttctctcta     300
aagttgtctt ctgtgactgc cgccgacaca ggcgtgtatt actgtgcctg ccgcagttac     360
gggaggaccc cgtactactt tgacttctgg ggccaaggca ccactctcac cgtctcctca     420
gctagc                                                                426

<210> SEQ ID NO 8
<211> LENGTH: 140
<212> TYPE: PRT
<213> ORGANISM: Artificial Sequence
<220> FEATURE:
<223> OTHER INFORMATION: IDEC-131 Humanized Variable Heavy Region 1

<400> SEQUENCE: 8

Met Met Val Leu Ser Leu Leu Tyr Leu Leu Thr Ala Leu Pro Gly Phe
 1               5                   10                  15

Leu Ser Glu Val Gln Leu Gln Glu Ser Gly Pro Gly Leu Val Lys Pro
            20                  25                  30

Ser Glu Thr Leu Ser Leu Thr Cys Thr Val Ser Gly Asp Ser Ile Thr
        35                  40                  45

Asn Gly Phe Trp Ile Trp Ile Arg Lys Pro Pro Gly Asn Lys Leu Glu
 50                  55                  60

Tyr Met Gly Tyr Ile Ser Tyr Ser Gly Ser Thr Tyr Tyr Asn Pro Ser
65                  70                  75                  80

Leu Lys Ser Arg Ile Ser Ile Ser Arg Asp Thr Ser Lys Asn Gln Phe
                85                  90                  95

Ser Leu Lys Leu Ser Ser Val Thr Ala Ala Asp Thr Gly Val Tyr Tyr
            100                 105                 110

Cys Ala Cys Arg Ser Tyr Gly Arg Thr Pro Tyr Tyr Phe Asp Phe Trp

```
              115                 120                 125
Gly Gln Gly Thr Thr Leu Thr Val Ser Ser Ala Ser
        130                 135                 140

<210> SEQ ID NO 9
<211> LENGTH: 411
<212> TYPE: DNA
<213> ORGANISM: Artificial Sequence
<220> FEATURE:
<223> OTHER INFORMATION: Anti-gp39 Vk sequence

<400> SEQUENCE: 9
agatctctca ccatgggctt caagatggag tcacagtttc tggcctttgt attcgcgttt      60
ctctggttgt ctggtgttga tggagacatt gtgatgaccc agtctcaaaa attcatgtcc     120
acatccgtag agacagggt cagcatcacc tgcaaggcca gtcagaatgt gattactgct      180
gtagcctggt atcaacagaa accaggacaa tctcctaaat tgctgattta ctcggcatcc     240
aatcggtaca ctggagtccc tgatcgcttc tcaggcagtg gtctgggac agatttcact     300 ctcaccatca gcaatatgca gtctgaagac ctggcagatt atttctgcca gcaatataac     360
agctatccgt acacgttcgg agggggggacc aagctggaaa tcaaacgtac g             411

<210> SEQ ID NO 10
<211> LENGTH: 133
<212> TYPE: PRT
<213> ORGANISM: Artificial Sequence
<220> FEATURE:
<223> OTHER INFORMATION: Anti-gp39 Vk sequence

<400> SEQUENCE: 10

Met Gly Phe Lys Met Glu Ser Gln Phe Leu Ala Phe Val Phe Ala Phe
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Ile Thr Cys Lys
        35                  40                  45

Ala Ser Gln Asn Val Ile Thr Ala Val Ala Trp Tyr Gln Gln Lys Pro
    50                  55                  60

Gly Gln Ser Pro Lys Leu Leu Ile Tyr Ser Ala Ser Asn Arg Tyr Thr
65                  70                  75                  80

Gly Val Pro Asp Arg Phe Ser Gly Ser Gly Ser Gly Thr Asp Phe Thr
                85                  90                  95

Leu Thr Ile Ser Asn Met Gln Ser Glu Asp Leu Ala Asp Tyr Phe Cys
            100                 105                 110

Gln Gln Tyr Asn Ser Tyr Pro Tyr Thr Phe Gly Gly Gly Thr Lys Leu
        115                 120                 125

Glu Ile Lys Arg Thr
    130

<210> SEQ ID NO 11
<211> LENGTH: 426
<212> TYPE: DNA
<213> ORGANISM: Artificial Sequence
<220> FEATURE:
<223> OTHER INFORMATION: Anti-gp39 Variable Heavy sequence

<400> SEQUENCE: 11
gtcgacatga tggtgttaag tcttctgtac ctgttgacag cccttccggg tttcctgtca      60
gaggtgcagc ttcaggagtc aggacctagc ctcgtgaaac cttctcagac tctgtccctc     120
```

```
acctgttctg tcactggcga ctccatcact aatggtttct ggatctggat ccggaaattc    180
ccagggaata aacttgagta catgggctac ataagttaca gtggtagcac ttactacaat    240
ccatctctca agagtcgaat ctccatcact cgcgacacat cccagaacca gttctaccta    300
caattgaatt ctgtgactac tgaggacaca ggcacatatt actgtgcctg ccgcagttac    360
gggaggaccc cgtactactt tgacttctgg ggccaaggca ccactctcac cgtctcctca    420
gctagc                                                                426
```

<210> SEQ ID NO 12
<211> LENGTH: 140
<212> TYPE: PRT
<213> ORGANISM: Artificial Sequence
<220> FEATURE:
<223> OTHER INFORMATION: Anti-gp39 Variable Heavy sequence

<400> SEQUENCE: 12

Met Met Val Leu Ser Leu Leu Tyr Leu Leu Thr Ala Leu Pro Gly Phe
1               5                   10                  15

Leu Ser Glu Val Gln Leu Gln Glu Ser Gly Pro Ser Leu Val Lys Pro
            20                  25                  30

Ser Gln Thr Leu Ser Leu Thr Cys Ser Val Thr Gly Asp Ser Ile Thr
        35                  40                  45

Asn Gly Phe Trp Ile Trp Ile Arg Lys Phe Pro Gly Asn Lys Leu Glu
    50                  55                  60

Tyr Met Gly Tyr Ile Ser Tyr Ser Gly Ser Thr Tyr Tyr Asn Pro Ser
65                  70                  75                  80

Leu Lys Ser Arg Ile Ser Ile Thr Arg Asp Thr Ser Gln Asn Gln Phe
                85                  90                  95

Tyr Leu Gln Leu Asn Ser Val Thr Thr Glu Asp Thr Gly Thr Tyr Tyr
            100                 105                 110

Cys Ala Cys Arg Ser Tyr Gly Arg Thr Pro Tyr Tyr Phe Asp Phe Trp
        115                 120                 125

Gly Gln Gly Thr Thr Leu Thr Val Ser Ser Ala Ser
    130                 135                 140

<210> SEQ ID NO 13
<211> LENGTH: 107
<212> TYPE: PRT
<213> ORGANISM: Artificial Sequence
<220> FEATURE:
<223> OTHER INFORMATION: IDEC-131 humanized variable light sequence 1

<400> SEQUENCE: 13

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asn Val Ile Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Tyr
                85                  90                  95

Thr Phe Gly Gly Gly Thr Lys Leu Glu Ile Lys

```
                100                 105

<210> SEQ ID NO 14
<211> LENGTH: 107
<212> TYPE: PRT
<213> ORGANISM: Artificial Sequence
<220> FEATURE:
<223> OTHER INFORMATION: IDEC-131 humanized variable light sequence 2

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asn Val Ile Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Asp Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: IDEC-131 humanized variable light sequence 3

<400> SEQUENCE: 15

Asp Ile Val Met Thr Gln Ser Pro Ser Phe Met Ser Thr Ser Val Gly
1               5                   10                  15

Asp Arg Val Thr Ile Thr Cys Lys Ala Ser Gln Asn Val Ile Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Asp Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: IDEC-131 humanized variable light sequence 4

<400> SEQUENCE: 16

Asp Ile Val Met Thr Gln Ser Pro Asp Ser Met Ala Thr Ser Leu Gly
1               5                   10                  15

Glu Arg Val Thr Ile Asn Cys Lys Ala Ser Gln Asn Val Ile Thr Ala
            20                  25                  30
```

```
Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Ser Gly
        50                  55                  60

Ser Gly Ser Gly Thr Asp Phe Thr Leu Thr Ile Ser Ser Met Gln Ala
65                  70                  75                  80

Glu Asp Val Ala Asp Tyr Phe Cys Gln Gln Tyr Asn Ser Tyr Pro Tyr
                85                  90                  95

Thr Phe Gly Gly Gly Thr Lys Leu Glu Ile Lys
            100                 105
```

```
<210> SEQ ID NO 17
<211> LENGTH: 11
<212> TYPE: PRT
<213> ORGANISM: Artificial Sequence
<220> FEATURE:
<223> OTHER INFORMATION: IDEC-131 humanized variable light chain CDR1

<400> SEQUENCE: 17

Lys Ala Ser Gln Asn Val Ile Thr Ala Val Ala
1               5                   10
```

```
<210> SEQ ID NO 18
<211> LENGTH: 7
<212> TYPE: PRT
<213> ORGANISM: Artificial Sequence
<220> FEATURE:
<223> OTHER INFORMATION: IDEC-131 humanized variable light chain CDR2

<400> SEQUENCE: 18

Ser Ala Ser Asn Arg Tyr Thr
1               5
```

```
<210> SEQ ID NO 19
<211> LENGTH: 9
<212> TYPE: PRT
<213> ORGANISM: Artificial Sequence
<220> FEATURE:
<223> OTHER INFORMATION: IDEC-131 humanized variable light chain CDR3

<400> SEQUENCE: 19

Gln Gln Tyr Asn Ser Tyr Pro Tyr Thr
1               5
```

```
<210> SEQ ID NO 20
<211> LENGTH: 120
<212> TYPE: PRT
<213> ORGANISM: Artificial Sequence
<220> FEATURE:
<223> OTHER INFORMATION: IDEC-131 humanized variable heavy chain
      sequence 1

<400> SEQUENCE: 20

Glu Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Asn Gly
            20                  25                  30

Phe Trp Ile Trp Ile Arg Lys Pro Pro Gly Asn Lys Leu Glu Tyr Met
            35                  40                  45

Gly Tyr Ile Ser Tyr Ser Gly Ser Thr Tyr Tyr Asn Pro Ser Leu Lys
        50                  55                  60

Ser Arg Ile Ser Ile Ser Arg Asp Thr Ser Lys Asn Gln Phe Ser Leu
```

```
                65                  70                  75                  80
Lys Leu Ser Ser Val Thr Ala Ala Asp Thr Gly Val Tyr Tyr Cys Ala
                    85                  90                  95

Cys Arg Ser Tyr Gly Arg Thr Pro Tyr Tyr Phe Asp Phe Trp Gly Gln
                    100                 105                 110

Gly Thr Thr Leu Thr Val Ser Ser
            115                 120

<210> SEQ ID NO 21
<211> LENGTH: 120
<212> TYPE: PRT
<213> ORGANISM: Artificial Sequence
<220> FEATURE:
<223> OTHER INFORMATION: IDEC-131 humanized variable heavy chain
      sequence 2

<400> SEQUENCE: 21

Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Asn Gly
                20                  25                  30

Phe Trp Ile Trp Ile Arg Lys His Pro Gly Asn Lys Leu Glu Tyr Met
            35                  40                  45

Gly Tyr Ile Ser Tyr Ser Gly Ser Thr Tyr Tyr Asn Pro Ser Leu Lys
        50                  55                  60

Ser Arg Ile Ser Ile Ser Arg Asp Thr Ser Lys Asn Gln Phe Ser Leu
65                  70                  75                  80

Lys Leu Ser Ser Val Thr Ala Ala Asp Thr Gly Val Tyr Tyr Cys Ala
                    85                  90                  95

Cys Arg Ser Tyr Gly Arg Thr Pro Tyr Tyr Phe Asp Phe Trp Gly Gln
                    100                 105                 110

Gly Thr Thr Leu Thr Val Ser Ser
            115                 120

<210> SEQ ID NO 22
<211> LENGTH: 120
<212> TYPE: PRT
<213> ORGANISM: Artificial Sequence
<220> FEATURE:
<223> OTHER INFORMATION: IDEC-131 humanized variable heavy chain
      sequence 3

<400> SEQUENCE: 22

Glu Val Gln Leu Gln Glu Ser Gly Pro Gly Leu Val Lys Pro Ser Gln
1               5                   10                  15

Thr Leu Ser Leu Thr Cys Ala Val Ser Gly Asp Ser Ile Thr Asn Gly
                20                  25                  30

Phe Trp Ile Trp Ile Arg Lys His Pro Gly Asn Lys Leu Glu Tyr Met
            35                  40                  45

Gly Tyr Ile Ser Tyr Ser Gly Ser Thr Tyr Tyr Asn Pro Ser Leu Lys
        50                  55                  60

Ser Arg Ile Ser Ile Ser Arg Asp Thr Ser Asn Asn Gln Phe Ser Leu
65                  70                  75                  80

Asn Leu Asn Ser Val Thr Arg Ala Asp Thr Gly Val Tyr Tyr Cys Ala
                    85                  90                  95

Cys Arg Ser Tyr Gly Arg Thr Pro Tyr Tyr Phe Asp Phe Trp Gly Gln
                    100                 105                 110

Gly Thr Thr Leu Thr Val Ser Ser
```

<210> SEQ ID NO 23
<211> LENGTH: 120
<212> TYPE: PRT
<213> ORGANISM: Artificial Sequence
<220> FEATURE:
<223> OTHER INFORMATION: IDEC-131 humanized variable heavy chain sequence 4

<400> SEQUENCE: 23

```
Glu Val Gln Leu Gln Glu Ser Gly Pro Gly Leu Val Lys Pro Ser Glu
1               5                   10                  15

Thr Leu Ser Leu Thr Cys Ala Val Tyr Gly Asp Ser Ile Thr Asn Gly
            20                  25                  30

Phe Trp Ile Trp Ile Arg Lys Pro Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Ser Arg Asp Thr Ser Lys Asn Gln Phe Tyr Leu
65                  70                  75                  80

Lys Leu Ser Ser Val Thr Ala Ala Asp Thr Gly Val Tyr Tyr Cys Ala
                85                  90                  95

Cys Arg Ser Tyr Gly Arg Thr Pro Tyr Tyr Phe Asp Phe Trp Gly Gln
            100                 105                 110

Gly Thr Thr Leu Thr Val Ser Ser
        115                 120
```

<210> SEQ ID NO 24
<211> LENGTH: 5
<212> TYPE: PRT
<213> ORGANISM: Artificial Sequence
<220> FEATURE:
<223> OTHER INFORMATION: IDEC-131 humanized variable heavy chain CDR1

<400> SEQUENCE: 24

```
Asn Gly Phe Trp Ile
1               5
```

<210> SEQ ID NO 25
<211> LENGTH: 16
<212> TYPE: PRT
<213> ORGANISM: Artificial Sequence
<220> FEATURE:
<223> OTHER INFORMATION: IDEC-131 humanized variable heavy chain CDR2

<400> SEQUENCE: 25

```
Tyr Ile Ser Tyr Ser Gly Ser Thr Tyr Tyr Asn Pro Ser Leu Lys Ser
1               5                   10                  15
```

<210> SEQ ID NO 26
<211> LENGTH: 12
<212> TYPE: PRT
<213> ORGANISM: Artificial Sequence
<220> FEATURE:
<223> OTHER INFORMATION: IDEC-131 humanized variable heavy chain CDR3

<400> SEQUENCE: 26

```
Arg Ser Tyr Gly Arg Thr Pro Tyr Tyr Phe Asp Phe
1               5                   10
```